(12) United States Patent
Shimizu et al.

(10) Patent No.: US 9,289,139 B2
(45) Date of Patent: Mar. 22, 2016

(54) BLOOD PRESSURE MONITOR

(75) Inventors: Hideki Shimizu, Saitama (JP); Yuichi Kato, Tokyo (JP)

(73) Assignees: CITIZEN HOLDINGS CO., LTD., Tokyo (JP); CITIZEN SYSTEMS JAPAN CO., LTD., Tokyo (JP)

(*) Notice: Subject to any disclaimer, the term of this patent is extended or adjusted under 35 U.S.C. 154(b) by 400 days.

(21) Appl. No.: 13/821,949

(22) PCT Filed: Sep. 9, 2011

(86) PCT No.: PCT/JP2011/071170
§ 371 (c)(1),
(2), (4) Date: Mar. 8, 2013

(87) PCT Pub. No.: WO2012/033232
PCT Pub. Date: Mar. 15, 2012

(65) Prior Publication Data
US 2013/0165800 A1 Jun. 27, 2013

(30) Foreign Application Priority Data
Sep. 9, 2010 (JP) ................................. 2010-201784

(51) Int. Cl.
*A61B 5/021* (2006.01)
*A61B 5/022* (2006.01)
(Continued)

(52) U.S. Cl.
CPC ............... *A61B 5/022* (2013.01); *A61B 5/021* (2013.01); *A61B 5/02438* (2013.01); *A61B 5/0507* (2013.01); *A61B 5/1107* (2013.01); *A61B 5/6824* (2013.01)

(58) Field of Classification Search
CPC .... A61B 5/721; A61B 5/0507; A61B 5/6824; A61B 2562/0228
USPC .......................................... 600/310, 485–499
See application file for complete search history.

(56) References Cited

U.S. PATENT DOCUMENTS 4,344,440 A * 8/1982 Aaby et al. ..................... 600/430
4,984,576 A 1/1991 Schulenberg et al.
(Continued)

FOREIGN PATENT DOCUMENTS

JP H08-215162 A 8/1996
JP 3297971 B 4/2002
(Continued)

OTHER PUBLICATIONS

International Search Report for PCT/JP2011/071170, Dec. 13, 2011.
(Continued)

*Primary Examiner* — Catherine B Kuhlman

(57) ABSTRACT

A method employed in a prior art arm-worn blood pressure monitor to measure the height position of the heart has been an indirect method that merely estimates the position of the heart, and therefore has had the problems that the measurement accuracy and the reliability of the measurement are low, and that the measuring position is awkward and it is difficult to achieve correct position alignment. An arm-worn blood pressure monitor includes a cuff, a microwave transmitting unit for radiating a microwave onto a human subject, a microwave receiving unit for receiving a reflected wave Doppler-shifted relative to the radiated microwave due to a heartbeat of the subject, and a correct position detector for detecting, based on the reflected wave, whether the cuff worn around an arm of the subject is located in a correct position relative to the position of the heart of the subject.

9 Claims, 10 Drawing Sheets

(51) Int. Cl.
    *A61B 5/024*     (2006.01)
    *A61B 5/05*     (2006.01)
    *A61B 5/11*     (2006.01)
    *A61B 5/00*     (2006.01)

(56) References Cited

U.S. PATENT DOCUMENTS

| | | | |
|---|---|---|---|
| 5,778,879 A * | 7/1998 | Ota et al. | 600/485 |
| 2002/0095092 A1 | 7/2002 | Kondo et al. | |
| 2004/0010199 A1 | 1/2004 | Hashimoto et al. | |
| 2011/0245695 A1 | 10/2011 | Kawano et al. | |

FOREIGN PATENT DOCUMENTS

| | | |
|---|---|---|
| JP | 2002-172095 A1 | 6/2002 |
| JP | 2003-325463 A | 11/2003 |
| JP | 2006-304963 A | 11/2006 |
| JP | 2010-142370 A | 7/2010 |

OTHER PUBLICATIONS

The State Intellectual Property Office of the People's Republic of China (SIPO), Office Action for Chinese Patent Application No. 201180043220.7, Aug. 28, 2014.

* cited by examiner

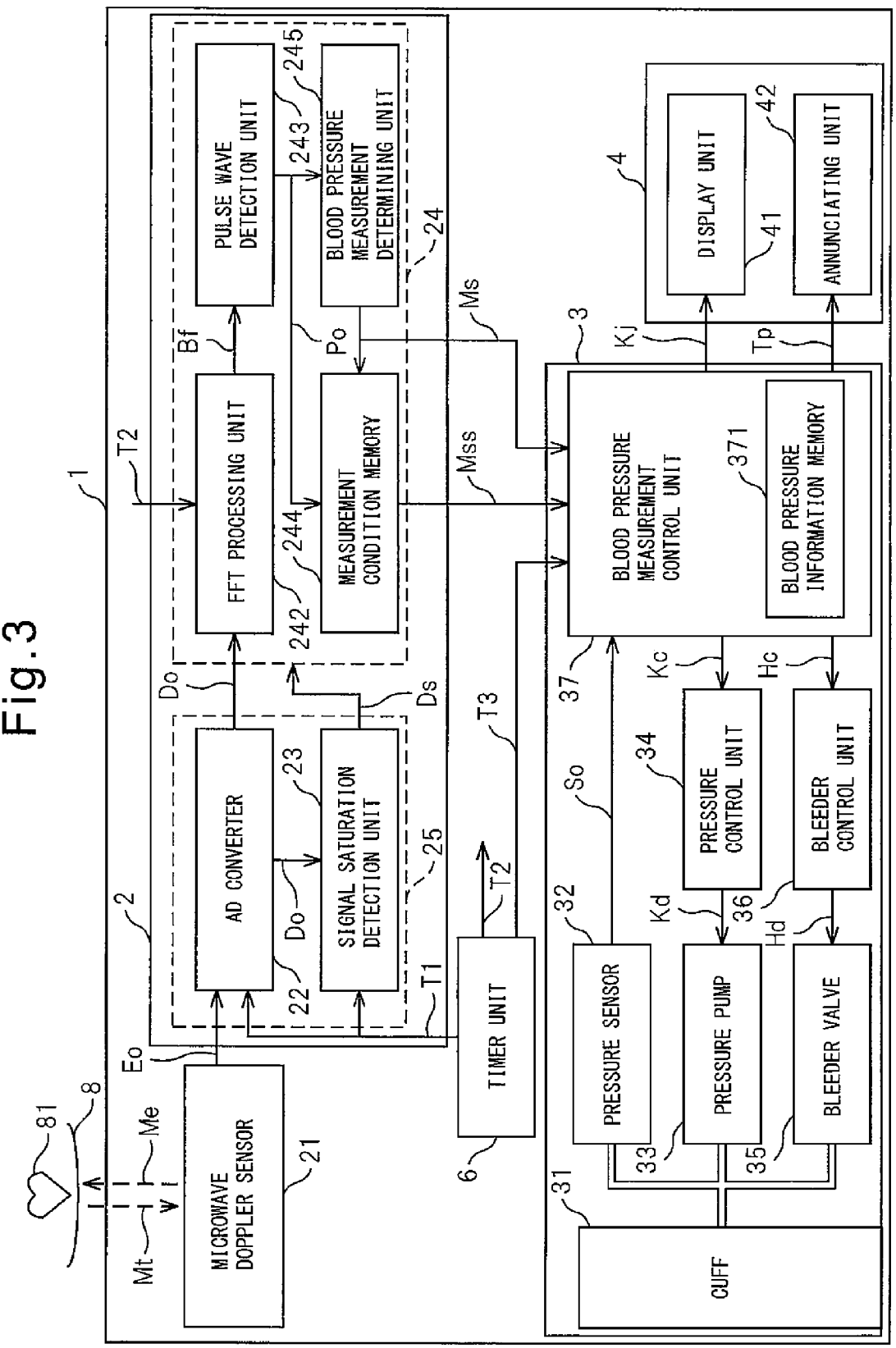

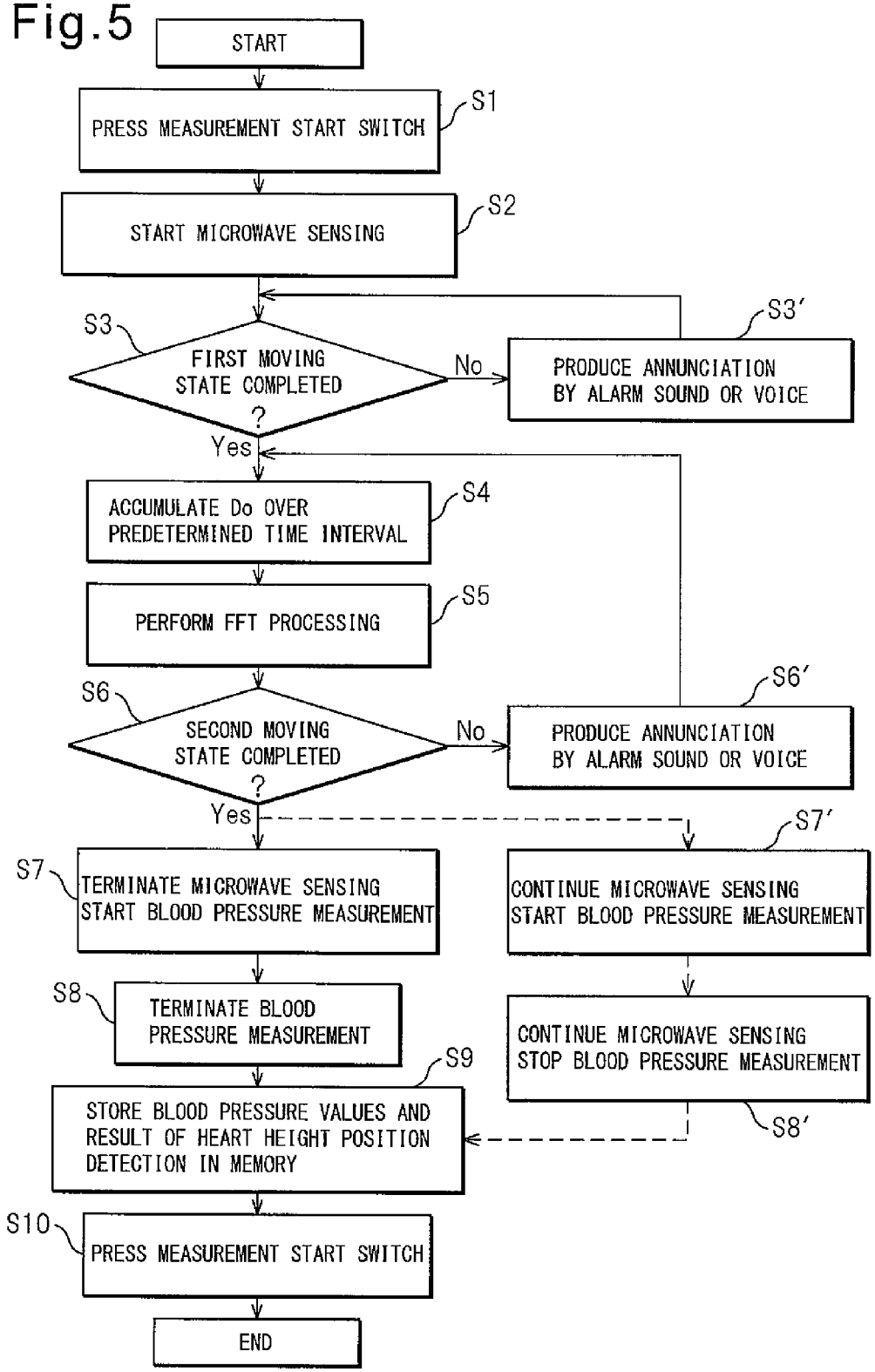

BLOOD PRESSURE MONITOR

TECHNICAL FIELD

The present invention relates to a blood pressure monitor worn on an arm for blood pressure measurement, and more specifically to a blood pressure monitor that can correctly align the position of the part to be measured for blood pressure with respect to the position of the heart.

BACKGROUND

Traditionally, blood pressure monitoring at home has only required that the results of blood pressure measurements be managed as part of daily health management, and has not required strict measurement results.

However, in recent years, the importance of daily health management has become important, and recent reports recommend that blood pressure be measured a plurality of times under 24-hour ambulatory conditions. By measuring blood pressure a plurality of times for a period of 24 hours, it is possible to monitor variations in blood pressure that could not be found by measuring blood pressure at an appropriate time within a day as would usually be done at home. That is, the basic idea behind the ambulatory blood pressure monitoring is that, by measuring blood pressure a plurality of times rather than only once, it is easier to discover a disease, etc., associated with variations in blood pressure.

For example, blood pressure is normally lower at night or during sleep, but it is reported that there are some hypertensive patients whose blood pressure does not fall even at night or during sleep. On the other hand, there are some whose blood pressure rises at night, which are prone to cerebral infarction, myocardial infarction, or the like, because high pressure continues to be exerted on the blood vessels during the night or during sleep when the pressure exerted on the blood vessels should normally fall. By monitoring variations in blood pressure within a day, it may is possible to detect not only hypertension but other diseases that are said to be related to hypertension.

Recently, terms such as masked hypertension, workplace hypertension, and white coat hypertension have come to be known and used widely. Masked hypertension is a phenomenon in which the blood pressure measured on a person is normal when actually the person is hypertensive.

Workplace hypertension is a form of masked hypertension. That is, when actually a person is hypertensive because the person is physically tired or mentally stressed due to work, the blood pressure measured at home, in a hospital, or in a workplace medical examination lies within the normal blood pressure range because the person is released from the fatigue or stress causes in such an environment. White coat hypertension is a phenomenon in which the blood pressure measured at home is normal but the blood pressure measured in a hospital exhibits a high blood pressure value.

Since white coat hypertension is induced by exposure to a hospital environment or at the sight of a white coat, it is said that the patient can recognize the symptom relatively easily. However, masked hypertension and workplace hypertension present the problem that not only the patient but also clinicians cannot easily recognize the hypertension because the hypertension is not reflected in the actually measured blood pressure values.

Such symptoms that are not easily recognizable even by the patient himself become easier to discover by monitoring variations in blood pressure within a day.

Generally, it is preferable that the blood pressure is measured with the patient in a relaxed state. If the patient is tense, the blood vessels contract and the blood pressure cannot be measured correctly. In view of this, it is often recommended that the patient breathe deeply or stay in a relaxed state for a few minutes before taking the blood pressure. It is therefore desirable, as a general rule, that the patient's physical and mental states at the time of blood pressure measurement be recorded together with the measured blood pressure values.

However, it is difficult to correctly measure and record the patient's physical and mental states. In view of this, some blood pressure monitors are designed to be able to measure pulse rate simultaneously with the blood pressure. By also measuring pulse rate, the patient's physical and mental states can be deduced from the recorded pulse rate. For example, if the pulse rate is high, it is deduced that the patient is under stress.

Further, when measuring the blood pressure, the positional relationship between the part on which the blood pressure is measured and the heart is also important. If the part on which the blood pressure is measured is not positioned correctly, the condition of the blood vessels in that part changes, resulting in an inability to correctly measure the blood pressure. For example, if the position of the part to be measured is lower than the position of the heart, the blood pressure may be measured higher than it really is. More specifically, it is said that the blood pressure rises by 7 mmHg as the position of the part to be measured becomes lower than the position of the heart by 10 cm.

When measuring the blood pressure, the part to be measured must be positioned at the same height as the heart. When a blood pressure measuring cuff is worn on the part to be measured, the position at which the cuff is at the same height as the heart is the correct position, and it is important to measure the blood pressure with the cuff held in the correct position. The correct position implies that the position of the part to be measured relative to the position of the heart is within the correct height range. The correct height range means that the part to be measured is positioned at approximately the same height as the heart, and does not mean that the former should be positioned strictly and exactly at the same height as the latter.

Recently, it has been recommended that the cuff be worn around the upper arm. This is because, first of all, the cuff or the like is easily worn around the upper arm, and also because the part to be measured can be easily held at the same height as the heart even when the patient lies on his back on the bed.

On the other hand, in the field of digital blood pressure monitors, a wrist-worn blood pressure monitor is known that measures blood pressure with the blood pressure monitor itself or the blood pressure measuring part worn on a wrist. Because of its structure, the wrist-worn blood pressure monitor can be made compact in size so that it is convenient to carry and suitable for blood pressure measurement in various environments such as home, workplace, etc. However, the wrist-worn blood pressure monitor requires that the part to be measured be positioned at the same height as the heart. In view of this, it is known to provide a blood pressure monitor in which a sensor is mounted in the blood pressure monitor itself or in the blood pressure monitoring part to detect the position of the part to be measured. For example, a wrist-worn blood pressure monitor is proposed that is equipped with an attitude detecting means constructed from a tilt sensor or the like (patent document 1).

The blood pressure monitor disclosed in patent document 1 will be described with reference to FIG. 10.

FIG. 10(a) is a diagram for explaining the tilting of the part to be measured by the wrist-worn blood pressure monitor disclosed in patent document 1 and the positional relationship of the part to be measured relative to the height position of the heart.

With the wrist-worn blood pressure monitor 112 worn on the wrist 111, the elbow 113 is placed on a desk 114; in this condition, the angle that the elbow 113 makes with the surface of the desk 114 is denoted by θ, and the difference in height between the heart 115 and the wrist-worn blood pressure monitor 112 is denoted by H. The relationship between the tilt θ and the height difference H is a linear function upward to the right, and if the tilt θ can be detected, the height difference H can be determined from the tilt θ.

That is, by detecting the degree of tilting of the wrist-worn blood pressure monitor 112 using a tilt sensor, and thereby obtaining the height position of the wrist-worn blood pressure monitor 112, the subject who is going to measure his blood pressure can hold the wrist-worn blood pressure monitor 112 in the correct position for measurement.

FIG. 10(b) is a diagram for explaining another example of the blood pressure monitor disclosed in patent document 1, illustrating how the position of the part to be measured is aligned with the position of the heart. In the illustrated example, the wrist-worn blood pressure monitor 112 has a built-in heartbeat sensor (more example, a microphone) 116, not a tilt sensor, and the wrist-worn blood pressure monitor 112 is brought close to the front part of the body near the heart to search for the correct position using the heartbeat sensor.

FIG. 10(c) is a graph depicting the strength of the heartbeat sound obtained by the heartbeat sensor 116 in the wrist-worn blood pressure monitor 112 when searching for the correct position as illustrated in FIG. 10(b). The strength of the heartbeat sound is plotted along the ordinate, and the position of the wrist-worn blood pressure monitor 112 is plotted as the scanning position along the abscissa. The wrist-worn blood pressure monitor 112 is pressed against the body of the subject and moved up and down to search the strength of the heartbeat obtained by the heartbeat sensor 116. The position of the heart is detected when the peak value Lp is detected, and the thus detected position is the correct position so far described.

In this way, the blood pressure monitor disclosed in patent document 1 detects the correct position by using the tilt sensor or the heartbeat sensor, after which the subject operates the start switch to start the blood pressure measurement.

Patent document 1: Japanese Patent No. 3297971 (pp. 2-3, FIGS. 2, 7, and 8).

SUMMARY

The method of FIG. 10(a) that measures the height position of the wrist-worn blood pressure monitor does not actually detect the position of the heart but merely judges by indirect means whether the wrist-worn blood pressure monitor is positioned at about the same height as the heart. Accordingly, the position alignment accuracy is poor, and the reliability of the blood pressure measurement is low. Furthermore, since the alignment is defined by the angle from the elbow, the subject is forced to hold an awkward position, resulting in it being difficult to correctly align the position with the correct position.

On the other hand, the method of FIGS. 10(b) and 10(c) that detects the position of the heart by using the heartbeat sensor requires that the wrist-worn blood pressure monitor 112 equipped with the built-in heartbeat sensor be brought close to the body part near the heart to directly search for the position of the heart. Since the heartbeat is detected using a microphone, the subject has to expose his chest by taking off his clothes. The inability to measure the blood pressure with the subject clothed greatly inconveniences the subject. Furthermore, since the heartbeat sensor is sensitive to external sound or noise of substantial magnitude, there has been the problem that the detection sensitivity drops, resulting in an inability to stably detect the peak value Lp corresponding to the position of the heart.

It is an object of the present invention to provide an arm-worn blood pressure monitor that is adapted to solve the above deficiencies.

It is also an object of the present invention to provide an arm-worn blood pressure monitor that can measure blood pressure with high reliability by correctly detecting the position of the heart.

An arm-worn blood pressure monitor includes a cuff, a microwave transmitting unit for radiating a microwave onto a human subject, a microwave receiving unit for receiving a reflected wave Doppler-shifted relative to the radiated microwave due to a heartbeat of the subject, and a correct position detector for detecting, based on the reflected wave, whether the cuff worn around an arm of the subject is located in a correct position relative to the position of the heart of the subject.

According to the above configuration, since the microwave that has the property of transmitting through clothes is reflected primarily by the heart that contains a large amount of blood, the correct position of the cuff relative to the position of the subject's heart can be detected with the subject clothed, and a highly reliable blood pressure measurement can thus be achieved.

Preferably, in the arm-worn blood pressure monitor, the correct position detector includes a second movement detector for detecting a second moving state in which the arm with the cuff worn therearound is being moved toward the correct position on the front part of a subject is chest.

By thus using the second movement detector, the correct position of the cuff on the front part of the chest can be detected, and a highly reliable blood pressure measurement can thus be achieved.

Preferably, in the arm-worn blood pressure monitor, the correct position detector includes a first movement detector for detecting a first moving state in which the arm with the cuff worn therearound is being moved toward the front part of the chest, wherein after it is determined by the first movement detector that the first moving state is completed, the second movement detector detects the second moving state.

By thus using two movement detector, the correct position of the cuff relative to the position of the subject's heart can be detected by correctly capturing the movement of the subject's arm around which the cuff is worn, and a highly reliable blood pressure measurement can thus be obtained.

Preferably, in the arm-worn blood pressure monitor, the first movement detector generates a phase difference signal representing a phase difference between a transmitted microwave signal corresponding to the microwave radiated by the microwave transmitting unit and a received microwave signal corresponding to the reflected wave received by the microwave receiving unit, and detects the first moving state by detecting from the phase difference signal any signal whose amplitude exceeds a prescribed amplitude range, and the second movement detector performs Fourier transform processing by accumulating over a predetermined time interval the phase difference signal whose amplitude does not exceed the prescribed amplitude range, extracts a fundamental wave of signal components, and detects the second moving state by extracting, as a pulse wave signal, components of the fundamental wave that fall within a prescribed frequency range.

According to the above configuration, the first moving state, which is supposed to involve a large motion, can be detected based on the amplitude of the phase difference signal, and the second moving state, which involves a relatively small motion from a position on the front part of the chest to the correct position, can be detected based on the pulse wave. Since the two different moving states can thus be detected appropriately by the respective detector, and the blood pressuring measuring part is aligned to the heart of the subject in the correct position, a highly reliable blood pressure measurement can be obtained.

Preferably, in the arm-worn blood pressure monitor, the first movement detector includes an AD converter for converting the phase difference signal into digital form for output, and a signal saturation state detector, wherein the AD converter converts the phase difference signal into a digital signal by sampling the phase difference signal based on first time information, and the signal saturation state detector counts, based on the digital signal, the number of occurrences of amplitude saturation exceeding the prescribed amplitude range bounded by a first saturation threshold value and a second saturation threshold value, wherein when the number of occurrences of the amplitude saturation is larger than a predetermined number, it is determined that the first moving state is in progress and, when the number of occurrences of the amplitude saturation decreases to zero after it is determined that the first moving state is in progress, it is determined that the first moving state is completed; also preferably, the second movement detector includes an FFT unit for performing the Fourier transform processing, and a pulse wave detector, wherein the FFT unit performs the Fourier transform processing by accumulating the digital signal over the predetermined time interval based on second time information, and thereby extracts the fundamental wave of signal components, and the pulse wave detector, based on the fundamental wave, extracts as the pulse wave the signal components that fall within the prescribed frequency range bounded by a first frequency threshold value and a second frequency threshold value, and determines, upon detection of the pulse wave, that the arm with the cuff worn therearound has been moved to the correct position.

According to the above configuration, the first moving state detector can detect the moving state based on the number of occurrences of the amplitude saturation, while the second moving state detector can detect the pulse wave based on whether the frequency (peak value) of the fundamental wave obtained by Fourier transforming lies within the frequency threshold range. Not only does this serve to increase the accuracy in detecting the pulse wave components of the subject, but it also becomes possible to output a blood pressure measurement start signal based on the detected pulse wave components, saving the trouble of performing an operation for starting the blood pressure measurement.

Preferably, in the arm-worn blood pressure monitor, the second movement detector further includes a blood pressure measurement determining unit for determining whether the arm with the cuff worn therearound is located in the correct position, and a blood pressure measuring unit, and when it is determined by the blood pressure measurement determining unit that the arm with the cuff worn therearound has been moved to the correct position, the blood pressure measuring unit starts blood pressure measurement.

According to the above configuration, when the blood pressure monitor is brought to the correct position, the blood pressure measurement can be started automatically, saving the subject the trouble of having to start the blood pressure measurement.

Preferably, in the arm-worn blood pressure monitor, if the arm with the cuff worn therearound is displaced from the correct position after the blood pressure measurement has been started, the blood pressure measuring unit stops the blood pressure measurement.

According to the above configuration, if the arm with the cuff worn therearound is displaced from the correct position after the blood pressure measurement has been started, there is no possibility of the pressure measurement being continued with the arm with the cuff worn therearound displaced from the correct position, and thus the reliability of the blood pressure measurement can be further enhanced.

Preferably, the arm-worn blood pressure monitor further includes a timer, a memory, and an alarm for annunciating information by means of a display, sound, light, vibration, or a combination thereof, wherein date/time information obtained from the timer, information related to the pulse wave, and a result of the blood pressure measurement are stored in the memory, and the contents stored in the memory are annunciated by using the alarm.

According to the above configuration, since the result of the blood pressure measurement as well as other information obtained during the measurement is stored and annunciated, not only the blood pressure of the subject but also the condition of the subject can be monitored.

Preferably, in the arm-worn blood pressure monitor, when it is determined by the blood pressure measurement determining unit that the arm with the cuff worn therearound has been moved to the correct position, the alarm means annunciates that the arm with the cuff worn therearound is located in the correct position.

According to the above configuration, if the arm with the cuff worn therearound is displaced from the correct position after the blood pressure measurement has been started, there is no possibility of the pressure measurement being continued with the arm with the cuff worn therearound displaced from the correct position, and thus the reliability of the blood pressure measurement can be further enhanced.

Preferably, in the arm-worn blood pressure monitor, the second movement detector extracts respiration information from the phase difference signal when detecting the second moving state, and stores the respiration information in the memory along with the date/time information obtained from the timer means, the information related to the pulse wave, and the result of the blood pressure measurement.

According to the above configuration, by also storing and annunciating the respiration information, not only the blood pressure of the subject but also the condition of the subject can be monitored in further detail.

According to the arm-worn blood pressure monitor, since the correct position of the blood pressure monitor relative to the position of the heart of the subject is detected accurately, if the blood pressure measuring part is worn on the arm, the blood pressure can be measured accurately.

BRIEF DESCRIPTION OF THE DRAWINGS

FIG. 3 is a functional block diagram showing the configuration of the arm-worn blood pressure monitor 1.

FIG. 5 is a flowchart illustrating the operation of the arm-worn blood pressure monitor 1 shown in FIG. 3.

DESCRIPTION OF EMBODIMENTS

Figure 1:
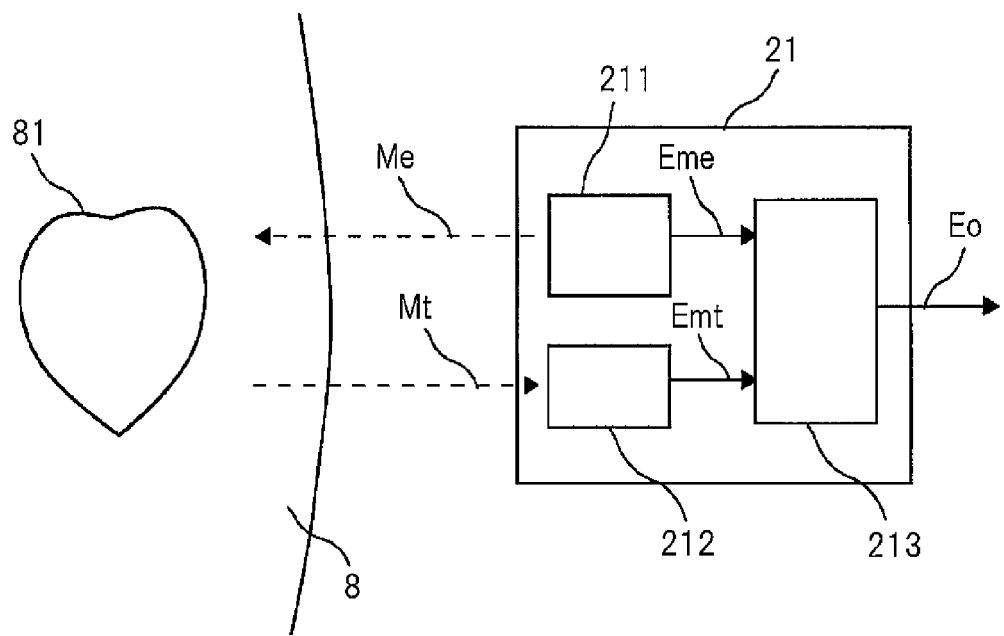
FIG. 1 is a schematic block diagram for explaining the basic principle of an arm-worn blood pressure monitor.

An arm-worn blood pressure monitor, using a microwave Doppler sensor, radiates a microwave onto the body of a human subject and receives the reflected wave to detect the correct position for the arm (the part to be measured) around which a cuff is worn for blood pressure measurement. In this way, the correction position for blood pressure measurement can be determined with the subject clothed, and the blood pressure can be measured correctly. The correct position here refers to the position at which the blood pressure monitor is at the same height as the heart, i.e., the position at which the part of the body to be measured for blood pressure is at the same height as the heart.

In addition, the pulse and respiration of the subject can also be measured from the reflected microwaves. In this way, not only can the blood pressure be measured, but the physically resting state or mentally stable state of the subject before the blood pressure measurement can be inferred from the pulse and respiration rates.

The arm-worn blood pressure monitor is unable to identify in which direction the subject's arm (for example, the wrist) around which the cuff of the arm-worn blood pressure monitor is worn is oriented relative to the subject's body (for example, whether the arm is lowered or raised) at the start of the blood pressure measurement. When the arm with the cuff worn therearound is being moved from this condition toward the correct position, the blood pressure monitor processes the signal obtained from the microwave Doppler sensor. A first movement detecting means detects a large movement of the arm based on the number of occurrences of amplitude saturation where the resulting signal exceeds a predetermined value. A second moving state detecting means detects whether the arm with the cuff worn therearound is located in the correct position by determining, based on the distribution of frequency components obtained by Fourier-transforming the resulting signal, whether the fundamental wave (peak value) falls within a prescribed frequency threshold range (i.e., whether the pulse and respiration have been detected correctly). Then, the pulse rate, respiration rate, etc., are recorded along with the measured blood pressure values so that the validity of the blood pressure measurement and the condition of the subject at that time can be verified anytime later.

The second moving state detecting means detects the pulse rate and respiration rate of the subject. In the case of the arm-worn blood pressure monitor shown in FIG. 3 to be described later, only the pulse rate is detected, while in the case of an alternative arm-worn blood pressure monitor to be described later with reference to FIG. 7, not only the pulse rate but the respiration rate is also detected. Pulse rate and respiration rate respectively have unique frequency components. Generally, the frequencies associated with pulses are higher than the frequencies associated with respiration. In view of this tendency, the frequency threshold range within which to select a peak value from the distribution of frequency components obtained by Fourier-transforming the signal generated by the microwave Doppler sensor is set so as to detect the pulse rate and the respiration rate, respectively, thereby making it possible to detect the pulse rate and the respiration rate.

By recording the pulse rate and respiration rate along with the date/time information of the blood pressure measurement, the condition of the subject at the time of the blood pressure measurement (more specifically, immediately before starting the blood pressure measurement) can be recorded in detail.

A major feature of the arm-worn blood pressure monitor is that the arm with the cuff worn therearound is placed in the correct position so that the blood pressure can be measured correctly. Furthermore, since the pulse-related information used when searching for the correct position can also be recorded, the validity of the blood pressure measurement can be verified anytime later, which is also a feature of this blood pressure monitor.

Since the pulse rate and respiration rate can thus be detected, the physically resting state or mentally stable state of the subject before the blood pressure measurement can be inferred from the pulse rate and respiration rate. Being able to record the condition of the subject along with the blood pressure values has an advantage because changes in the physically resting state or mentally stable state of the subject can be kept track of, for example, when examining variations in the blood pressure measured a plurality of times under 24-hour ambulatory conditions.

The arm-worn blood pressure monitor will be described below with reference to drawings. It will, however, be noted that the technical scope of the present invention is not limited to any specific embodiment described herein but extends to the inventions described in the appended claims and their equivalents.

In the arm-worn blood pressure monitor, the cuff worn around the designated part of the human body for blood pressure measurement may be provided separately from or integrated with the main body of the blood pressure monitor in which a blood pressure control unit, annunciating means, etc., are mounted, the only requirement being that the cuff and the microwave Doppler sensor be combined in one unit. The following description will be given by taking as an example the configuration in which the cuff, the microwave Doppler sensor, and the main body of the blood pressure monitor are combined in one unit.

The arm-worn blood pressure monitor 1 will be described in detail below with reference to FIGS. 1 to 6. The following description will be given by taking as an example the case where the arm-worn blood pressure monitor is worn principally on the wrist of the left arm.

FIG. 1 is a schematic block diagram for explaining the basic principle of the arm-worn blood pressure monitor. Referring to FIG. 1, a detailed description will be given of how the microwave Doppler sensor can detect whether the arm-worn blood pressure monitor 1 is in the correct position relative to the heart of the subject.

In FIG. 1, the microwave Doppler sensor 21 includes a microwave transmitter 211 which transmits a microwave, for example, of about 2.5 GHz, a microwave receiver 212 which receives the transmitted microwave, and a microwave Doppler demodulator 213.

A conventional microwave Doppler sensor may be used as the microwave Doppler sensor here. There are two types of microwave Doppler sensors, one for outputting an analog signal and the other for outputting a digital signal, and either type may be used. In the example of FIG. 1, the signal output from the microwave Doppler demodulator 213 is an analog signal, and the microwave Doppler sensor 21 is not mounted with an AD converter that converts the analog signal into a digital signal.

A portion of the microwave Me transmitted from the microwave transmitter 211 enters the body of the subject 8 and is reflected by the heart 81, and the reflected wave Mt emerging from the body of the subject 8 is received by the microwave receiver 212. The microwave transmitter 211 outputs a transmitted microwave signal Eme which is an electrical signal corresponding to the transmitted microwave Me. The microwave receiver 212 outputs a received microwave signal Emt which is an electrical signal corresponding to the received reflected microwave Mt.

The microwave Doppler demodulator 213 takes the transmitted microwave signal Eme and the received microwave signal Emt as inputs, and outputs an electrical signal Eo representing the phase difference between the two input signals.

Due to the Doppler shift associated with the motion of the heart, the reflected wave Mt received by the microwave receiver 212 is shifted in phase relative to the microwave Me transmitted from the microwave transmitter 211. The microwave phase difference due to the Doppler shift, taken between the transmitted microwave signal Eme and the received microwave signal Emt, is converted by the microwave Doppler demodulator 213 into the electrical signal Eo, thereby making it possible to detect the motion of the heart.

FIG. 2 is a diagram for explaining a sequence of arm movements.

FIGS. 2(a) to 2(e) are diagrams schematically illustrating how the left arm 8a of the subject 8, with the arm-worn blood pressure monitor 1 worn on the wrist thereof, is moved until it gets ready for blood pressure measurement. FIG. 2(f) is a diagram, showing the subject as viewed from the top thereof, for explaining the front part of the subject's chest.

Figure 2A:
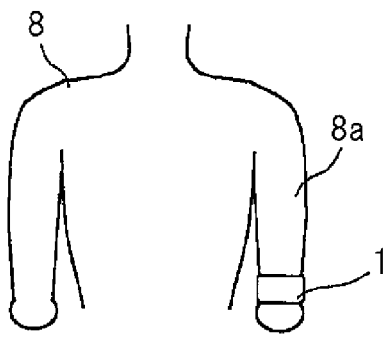
FIG. 2 is a diagram for explaining a sequence of arm movements.
Figure 2B:
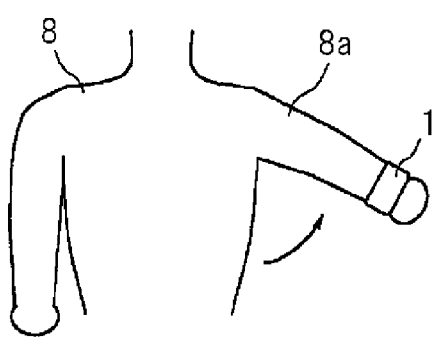

FIG. 2(a) shows a condition in which the arm-worn blood pressure monitor 1 is worn and a switch not shown is operated to start the blood pressure measurement. For example, the arm-worn blood pressure monitor 1 is worn on the wrist of the subject's left arm, and the switch on an operation unit (not shown) is operated with his right hand. FIGS. 2(b) and 2(b) are diagrams showing the first moving state of the arm (with the arm-worn blood pressure monitor worn thereon). The subject slowly moves his left hand, as indicated by arrow in FIG. 2(b), and thus brings the arm-worn blood pressure monitor 1 to the front part 8b of the chest of the subject 8, as indicated by arrow in FIG. 2(c).

The front part 8b of the chest here includes the front part of the body, as shown in FIG. 2(f). Since the heart is usually located in the left part of the chest or slightly to the right, the left part of the chest is the position suitable for detecting the beating of the heart. However, the microwave Doppler sensor 21 can detect the heartbeat if the sensor is not positioned exactly on the front of the left part of the chest. For example, the heartbeat can be detected if the sensor is positioned obliquely to the left of the left part of the chest (for example, on the left flank of the body or the side under the left arm) or on the center of the chest; depending on the subject, the heartbeat can be detected even on the front of the right part of the chest. Accordingly, the "front part of the chest" is defined as the area of the front part 8b of the chest shown in FIG. 2(f).

Figure 2C:
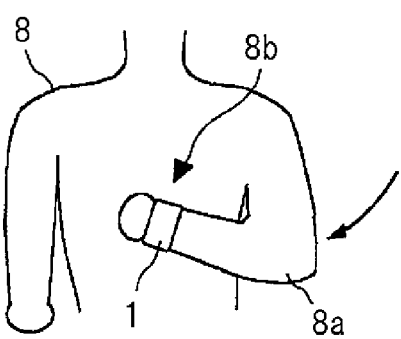
Figure 2D:
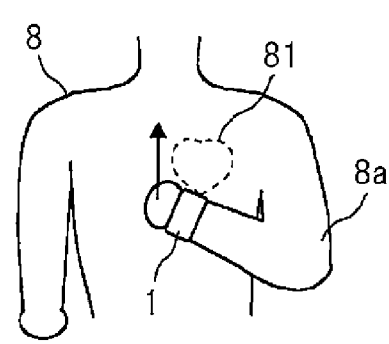
Figure 2E:
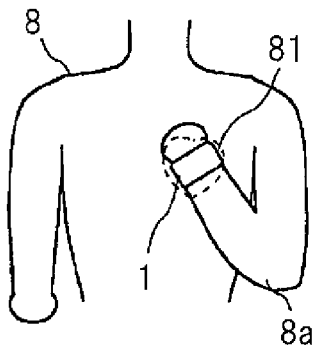
Figure 2F:
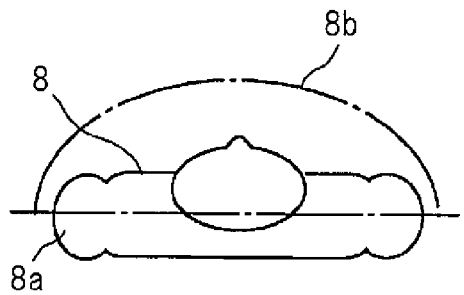

FIG. 2(d) is a diagram showing the second moving state in progress. The subject further moves his arm until the arm-worn blood pressure monitor 1 positioned on the front part 8b of the chest as shown in FIG. 2(c) is brought to the correct position located at the same height as the heart 81, as indicated by arrow in FIG. 2(d). FIG. 2(e) shows a condition in which the arm-worn blood pressure monitor 1 is brought to the correct position located at the same height as the heart 81.

When the arm-worn blood pressure monitor 1 is in the first moving state, the arm-worn blood pressure monitor 1 is being moved with a large arm motion. On the other hand, in the second moving state, the arm-worn blood pressure monitor 1 is being moved with a small arm motion. Though the details will be described later, in the first moving state, the first moving state is detected based on the amplitude of the electrical signal Eo output from the microwave Doppler sensor 21 shown in FIG. 1, while in the second moving state, a pulse wave is detected based on the signal frequency components contained in the electrical signal Eo, and the correct position is located based on the pulse wave. In this way, in the arm-worn blood pressure monitor 1, the amplitude and frequency of the electrical signal output from the microwave Doppler sensor are used to detect the respective moving states.

In the description given herein, the method of detecting the motion of the body from the electrical signal Eo by using the microwave Doppler sensor 21 will be referred to simply as "microwave sensing".

FIG. 3 is a functional block diagram for explaining the configuration of the arm-worn blood pressure monitor 1.

In FIG. 3, the arm-worn blood pressure monitor 1 includes a correct position detecting means 2 for detecting whether a part to be measured for blood pressure is positioned correctly relative to the height position of the heart, a blood pressure measuring means 3 for measuring blood pressure, an annunciating means 4 which includes a display unit 41 for visually displaying measurement results and an annunciating unit 42 for producing an audible annunciation by means of an alarm sound or voice, and a timer unit 6 which generates time information such as date/time information. The same component elements as those already described are designated by the same reference numerals.

First, the configuration of the correct position detecting means 2 will be described.

As shown in FIG. 3, the correct position detecting means 2 includes a first movement detecting means 25 and a second movement detecting means 24. The first movement detecting means 25 includes an AD converter 22 and a signal saturation detection unit 23. The AD converter 22 a converter which, based on first time information from the timer unit 6, converts the electrical signal Eo output from the microwave Doppler sensor 21 into a digital signal Do. The signal saturation detection unit 23 detects saturation of the digital signal Do and outputs a first moving state completion signal Ds indicating the completion of the first moving state. The second movement detecting means 24 includes an FFT (Fast Fourier Transform) processing unit 242, a pulse wave detection unit 243, a blood pressure measurement determining unit 245, and a measurement condition memory 244.

The FFT processing unit 242 performs FFT processing by accumulating the digital signal Do over a predetermined time interval based on second time information T2 supplied from the timer unit 6, and outputs a fundamental wave Bf as frequency spectrum information. The pulse wave detection unit 243 takes the fundamental wave Bf as input and outputs pulse wave data Po. The blood pressure measurement determining unit 245 takes the pulse wave data Po as input and outputs a correct position detection signal Ms.

The measurement condition memory 244 stores the pulse wave data Po and the correct position detection signal Ms as needed, and outputs a correct position memory signal Mss.

The timer unit 6 includes, though not shown, a source clock unit which outputs a clock signal of a prescribed frequency by using a crystal oscillator or the like, a frequency dividing circuit which generates a given frequency-divided signal by frequency-dividing the clock signal, and a time generating unit which generates time information from the frequency-divided signal. This configuration is well known for a timer circuit or the like, and therefore, a detailed description will not be given here.

The first time information T1, second time information T2, and third time information T3 are output from the timer unit 6. The first time information T1 carries time information for determining the sampling time of the AD converter 22, and is, for example, a signal whose pulse period is 10 msec. The second time information T2 carries time information for acquiring the predetermined time interval over which the digital signal Do is to be accumulated in the FFT unit, and is, for example, a signal whose pulse period is 10 to 30 sec. The third time information T3 carries information indicating the date and time of the blood pressure measurement.

Next, the configuration of the blood pressure measuring means 3 will be described.

The blood pressure measuring means 3 include a cuff 31, a pressure sensor 32, a pressure pump 33, a pressure control unit 34, a bleeder valve 35, a bleeder control unit 36, and a blood pressure measurement control unit 37.

The cuff 31 is a belt-like member for applying pressure to the radial artery on the wrist to impede the blood flow therein. The pressure sensor 32 converts the pressure of the cuff 31 into an electrical signal which is output as a pressure signal So. The pressure pump 33 is a pump for inflating the cuff 31. The pressure control unit 34 outputs a pressure drive signal Kd, based on a pressure control signal Kc from the blood pressure measurement control unit 37, to drive the pressure pump 33.

The bleeder valve 35 is a valve for reducing the pressure from the cuff 31 at a prescribed rate. The bleeder control unit 36 controls the bleeder valve 35 by outputting a bleeder drive signal Hd based on a bleeder control signal Hc supplied from the blood pressure measurement control unit 37.

The blood pressure measurement control unit 37 controls and manages the entire operation of the arm-worn blood pressure monitor 1. More specifically, the blood pressure measurement control unit 37 outputs blood pressure information Kj and a correct position annunciation signal Tp, based on the pressure signal So, the correct position detection signal Ms and, if necessary, the correct position memory signal Mss. The blood pressure information Kj is information that carries values such as the systolic blood pressure, diastolic blood pressure, and pulse rate, as well as the date/time information of the blood pressure measurement and the correct position detection signal Ms. The correct position annunciation signal Tp is correct position information comprised of the correct position detection signal Ms. The blood pressure measurement control unit 37 includes a blood pressure information memory 371 as a means for storing the blood pressure information Kj. The blood pressure measurement control unit 37 is not limited to any specific configuration, but it includes at least a CPU and a memory. It is advantageous to construct the blood pressure measurement control unit 37 using a one-chip microcomputer or the like, because the size and power consumption can then be reduced.

Next, the configuration of the annunciating means 4 will be described with reference to FIGS. 3 and 6.

The annunciating means 4 includes the display unit 41 and the annunciating unit 42. The display unit 41 displays the blood pressure information Kj, such as the systolic blood pressure, diastolic blood pressure, pulse rate, and blood pressure measurement date/time information, that the blood pressure measurement control unit 37 outputs. The annunciating unit 42 produces an annunciation by means of voice, sound, or vibration to indicate to the subject whether or not the blood pressure measuring part of the arm-worn blood pressure monitor 1 is located in the correct measurement position.

FIG. 6 is a diagram for explaining, by way of example, how the annunciating means 4 produces an annunciation. The annunciating means 4 is a means for annunciating whether or not the blood pressure measuring part of the arm-worn blood pressure monitor 1 is located in the correct position at the same height as the heart, and for displaying the measured blood pressure values.

As shown in FIG. 6, the display unit 41 includes a systolic blood pressure display section 411, a diastolic blood pressure display section 412, a pulse rate display section 413, a measurement condition display section 415 which includes a pulse condition display section 415a, and a date/time display section 416 for displaying information indicating the date and time of blood pressure measurement, and displays the blood pressure information Kj, including the systolic blood pressure, diastolic blood pressure, pulse rate, and correct position detection signal Ms, that the blood pressure measurement control unit 37 in the blood pressure measuring means 3 outputs.

The pulse condition display section 415a produces an indication using a mark or light according to the level of the correct position detection signal Ms. For example, when the correct position detection signal Ms has three different levels, the indication is produced by using different marks for different levels, such as "O" for level 3 when the position is in the correct position, "Δ" for level 2 when it is slightly displaced from the correct position, and "X" for level 1 when it is substantially displaced from the correct position.

The three levels can be defined, for example, in the following manner. The level 3 that indicates that the position is in the correct position is produced when the blood pressure measuring part of the arm-worn blood pressure monitor 1 is located within the range of less than ±1 cm from the right atrium. The level 2 that indicates that the position is slightly displaced from the correct position is produced when the blood pressure measuring part of the arm-worn blood pressure monitor 1 is located within the range from ±1 cm to less than ±5 cm from the right atrium. The level 1 that indicates that the position is substantially displaced from the correct position is produced when the blood pressure measuring part of the arm-worn blood pressure monitor 1 is located ±5 cm or more away from the right atrium. Each of the above levels is produced by setting a threshold value for the amplitude of the digital signal Do or pulse wave data Po for that level and by determining whether the threshold value is exceeded or not. The above levels may be indicated using different LED light colors. For example, the level 3 may be indicated by "blue", the level 2 by "yellow", and the level 1 by "red". It is of course possible to produce the indication by combining a mark and light.

Figure 6A:
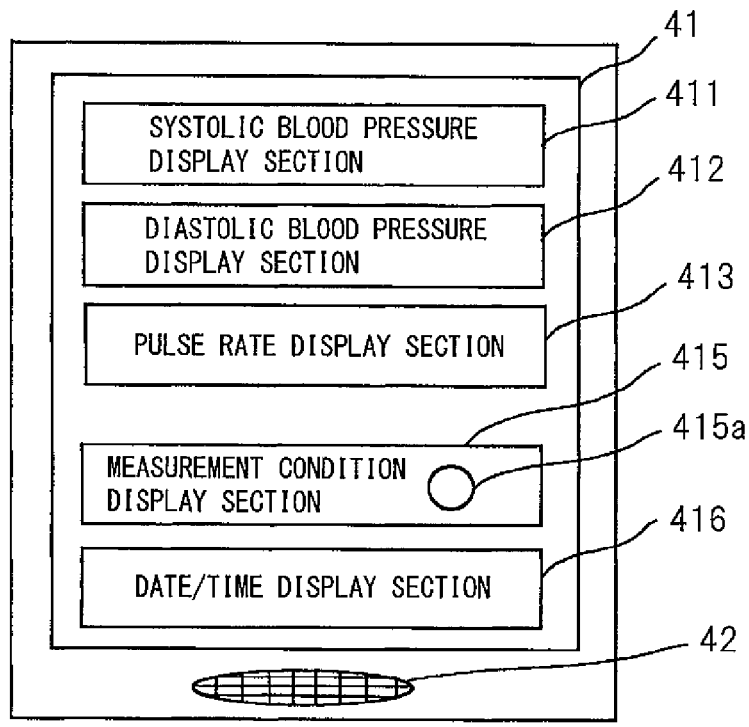
FIGS. 6(a) and 6(b) are diagrams for explaining display examples produced on the arm-worn blood pressure monitor 1 shown in FIG. 3.
Figure 6B:
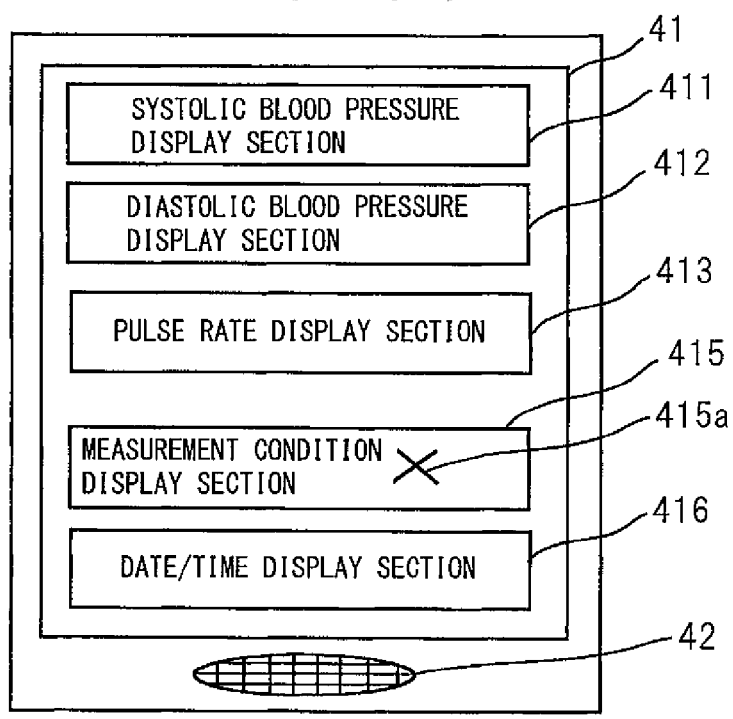

In the example of FIG. 6, whether the position is in the correct position or not is indicated using a mark. FIG. 6(a) shows an example of the display produced when the correct position detection signal Ms is of level 3 which is indicated by the mark "O". FIG. 6(b) shows an example of the display produced when the correct position detection signal Ms is of level 1 which is indicated by the mark "X".

In the example shown in FIG. 6, the systolic blood pressure display section 411, diastolic blood pressure display section 412, pulse rate display section 413, measurement condition display section 415, and date/time display section 416 of the display unit 41 are shown as being separate, independent display units, but the display unit 41 may be constructed from a single liquid crystal display unit whose display area is divided into the respective display sections.

The annunciating unit 42 is constructed from a dynamic speaker or a piezoelectric acoustic device, and produces an annunciation by means of an alarm sound or voice. In the case of voice, a message may be produced which says, for example, "The blood pressure monitor is in the correct position" or "The blood pressure monitor is not in the correct position". By thus being guided by the light, mark, or voice, the subject can properly bring the arm-worn blood pressure monitor into the correct position.

As is known, it is recommended that the blood pressure be measured with the subject in a relaxed state. Accordingly, when the arm-worn blood pressure monitor 1 is brought to the front part of the chest, if the subject can be alerted by means of an alarm sound or voice as described above, the subject need not turn his head down to confirm the condition, etc. and can maintain the relaxed position, which is advantageous.

Since the arm-worn blood pressure monitor 1 can also measure the pulse rate, the condition of the subject at the time of blood pressure measurement can be recorded along with the measured blood pressure values. Then, the subject can check the recorded information anytime by using the annunciating means. Since the blood pressure and the condition of the subject can be managed in this way, it may be possible to keep track of the medical condition of the subject and detect masked hypertension, etc.

Next, the operation of the arm-worn blood pressure monitor 1 will be described with reference to FIGS. 3 and 4.

First, the operation of the correct position detecting means 2 will be described.

In FIG. 3, the subject 8 with the arm-worn blood pressure monitor 1 worn on his wrist (not shown) presses the measurement start switch on the operation unit, whereupon the microwave Doppler sensor 21 transmits the microwave Me of about 2.5 GHz. The transmitted microwave Me is reflected by striking on the subject 8, and the reflected wave Mt is received by the microwave receiver 212.

The electrical signal Eo, produced by the microwave Doppler sensor 21 based on the transmitted microwave signal Eme corresponding to the microwave Me and the received microwave signal Emt based on the reflected wave Mt, is supplied to the AD converter 22 in the first movement detecting means 24. The details of the operation of the microwave Doppler sensor 21 have previously been described with reference to FIG. 1.

The AD converter 22 converts the electrical signal Eo into a time-series digital signal Do which is supplied to the signal saturation detection unit 23 as well as to the second movement detecting means 24.

When the amount of variation of the input digital signal Do exceeds a prescribed amplitude range to be described later a predetermined number of times, the signal saturation detection unit 23 outputs the first moving state completion signal Ds to the second movement detecting means 24. In this case, the first moving state completion signal Ds from the signal saturation detection unit 23 may be input to the blood pressure measurement control unit 37. Then, based on the first moving state completion signal Ds, the blood pressure measurement control unit 37 controls the annunciating means 4 to annunciate the completion of the first moving state by means of sound, light, or voice.

When the digital signal Do is input, the second movement detecting means 24 outputs the correct position detection signal Ms to the blood pressure measuring means 3. The FFT processing unit 242 in the second movement detecting means 24 performs FFT by accumulating the digital signal Do over a predetermined time interval in accordance with the second time information T2. The FFT involves applying a fast Fourier transform to the input signal. More specifically, after the accumulated digital signal Do is Fourier-transformed and decomposed into its constituent signal components, processing is performed to arrange each component in a frequency spectrum, and the result is output as the fundamental wave Bf to the pulse wave detection unit 243.

The pulse wave detection unit 243 takes the fundamental wave Bf as input, extracts from the fundamental wave Bf the components in the frequency band associated with the pulses, and outputs them as the pulse wave data Po to the measurement condition memory 244 and the blood pressure measurement determining unit 245.

The operation of the signal saturation detection unit 23 in the first movement detecting means 25 and the operation of the second movement detecting means 24 will be further described with reference to FIGS. 2 and 4.

Figure 4A:
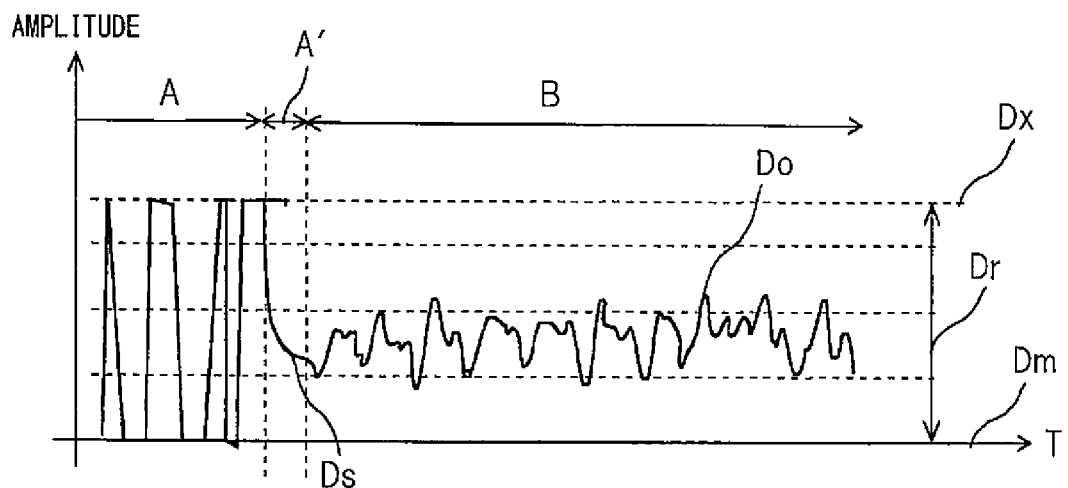
FIGS. 4(a) to 4(c) are waveform diagrams for explaining the operation of the arm-worn blood pressure monitor 1 shown in FIG. 3.

FIG. 4 is a diagram schematically illustrating waveforms for explaining the operation of the first movement detecting means 25 and second movement detecting means 24 in the correct position detecting means 2. In FIG. 4(a), the time T is plotted along the abscissa and the amplitude of the digital signal Do along the ordinate, and the waveform shows how the digital signal Do, i.e., the signal output from the microwave Doppler sensor 21, changes over time.

In FIG. 4(a), an interval A represents the time interval during which the subject 8 brings the arm-worn blood pressure monitor 1 toward his chest after wearing the arm-worn blood pressure monitor 1 on his wrist and pressing the measurement start switch on the operation unit. This represents the first moving state shown in FIGS. 2 (a) to 2(c).

In FIG. 4(a), Dx indicates a first saturation threshold value, and Dm indicates a second saturation threshold value. The prescribed amplitude range Dr is defined by the difference between the first saturation threshold value Dx and the second saturation threshold value Dm. On the other hand, Ds is the first moving state completion signal. Predetermined threshold values may be used as the first saturation threshold value Dx and the second saturation threshold value Dm, respectively. The prescribed amplitude range Dr is set by using the two threshold values. In the example shown in FIG. 4(a), the second saturation threshold value Dm is zero, i.e., the so-called zero saturation threshold value, which together with the first saturation threshold value Dx set at a prescribed amplitude value (the so-called positive saturation threshold value), defines the prescribed amplitude range Dr.

In the interval A (the first moving state), since the effect of the moving arm is added to the microwave reflected by the body surface of the subject 8, the Doppler shift increases, and the amplitude of the digital signal Do abruptly increases. The signal saturation detection unit 23 in the first movement detecting unit 25 counts the number of times that the amplitude of the digital signal Do exceeds the prescribed amplitude range Dr. When the prescribed amplitude range Dr has been exceeded more than a predetermined number of times, the signal saturation detection unit 23 detects that the first moving state is in progress. The predetermined number is set in advance by selecting a suitable number through experiment, etc. For example, suppose that the predetermined number is 10; then, when the amplitude of the digital signal Do has exceeded the prescribed amplitude range Dr 10 times, it is detected that the first moving state is in progress.

In FIG. 4(a), an interval A' corresponds to the ending portion of the interval A and represents the time when the first moving state is completed. As earlier described with reference to FIGS. 2(a) to 2(c) and FIG. 2(f), the first moving state in which the arm of the subject 8 is being moved with a large motion toward the front part 8b of his chest is completed when the arm-worn blood pressure monitor 1 comes to a position near the heart in the front part 8b of the chest as shown in FIG. 2(c). That is, when the digital signal Do comes to settle within the prescribed amplitude range Dr in the interval A', it is determined that the arm is no longer being moved with a large motion, i.e., the first moving state is completed. The digital signal Do at this time is detected as the first moving state completion signal Ds.

The second movement detection means 24 performs signal processing by taking as input the digital signal Do output from the first movement detection means 25, but does not start the processing until the first moving state completion signal Ds is received. This is to prevent the signal processing from being started when the first moving state is not yet completed.

In FIG. 4(a), an interval B represent the time interval during which the wrist is placed and held in position near the heart. This time interval represents the second moving state shown in FIGS. 2(d) and 2(e). In the interval B, since the arm is no longer being moved with a large motion but is being moved with a small motion in order to search for the correct position, the digital signal Do whose amplitude falls within the prescribed amplitude range Dr is detected. The waveform in this interval B contains a waveform associated with the beating of the heart.

Figure 4B:
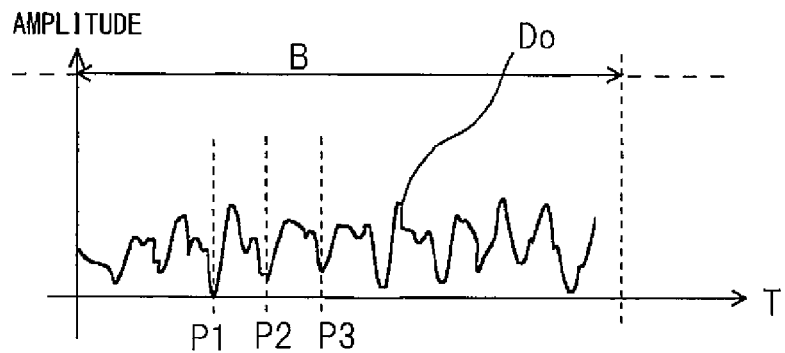

FIG. 4(b) is a diagram showing in enlarged form a portion of the digital waveform Do in the interval B depicted in FIG. 4(a). The time interval shown here is designated as interval D. The digital signal Do shown here contains the heartbeat components (for example, P1, P2, and P3) detected on the subject 8.

Figure 4C:
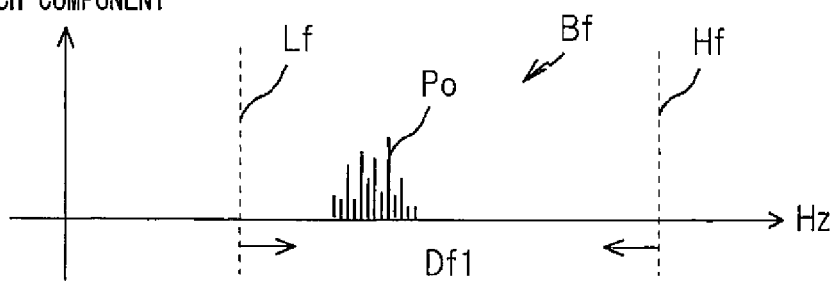

FIG. 4(c) is a diagram schematically illustrating the waveform obtained by fast-Fourier transforming the digital signal Do by the FFT processing unit 242. A frequency spectral distribution diagram is shown with the frequency plotted along the X axis and the signal strength of each frequency component along the Y axis. In the interval B shown in FIG. 4(a), the FFT processing unit 242 performs the fast Fourier transform by accumulating the digital signal Do over a predetermined time interval in accordance with the second time information T2, and obtains the fundamental wave Bf of the frequency components such as shown in FIG. 4(c).

The pulse wave detection unit 243 in the second movement detecting means 24 computes the pulse wave data Po from a prescribed frequency range of the fundamental wave Bf. In FIG. 4(c), Lf is a first frequency threshold value, and Hf is a second frequency threshold value. The range bounded by the first frequency threshold value Lf and the second frequency threshold value Hf is the prescribed frequency range Df1. This frequency range must be set so as to be able to capture the pulse wave. According to the result of the experiment conducted by the present inventor, when the first frequency threshold value Lf is set at 0.5 Hz and the second frequency threshold value Hf at 3.0 Hz, the pulse wave can be captured. These values are only examples, and the first frequency threshold value Lf and the second frequency threshold value Hf are not limited to any specific values.

The pulse wave detection unit 243 outputs the pulse wave data Po by extracting the frequency spectral distribution contained in the prescribed frequency range Df1 of the fundamental wave Bf. When the pulse wave data Po is detected properly, the second moving state is completed. At this time, the arm-worn blood pressure monitor 1 is located in the correct position at the same height as the heart 81, as shown in FIG. 2(e).

The blood pressure measurement determining unit 245 analyzes the received pulse wave data Po. Since the pulse wave data Po represents the spectral distribution of the frequency components, statistical processing such as the computation of frequency components or power intensity or mean, variance, standard deviation, etc. can be performed. When the result of the processing satisfies the condition suitable for blood pressure measurement, the correct position detection signal Ms is supplied to the blood pressure measuring means 3.

As shown in FIG. 4(c), the frequency spectral distribution contained in the prescribed frequency range Df1 provides the pulse wave data Po. Therefore, if the first frequency threshold value Lf and the second frequency threshold value Hf are suitable threshold values, the waveform suitable as the pulse wave is invariably contained in that range. The peak of each waveform contained in the pulse wave data Po, for example, may be calculated by statistical processing, and the pulse wave may be determined, for example, based on the tendency of occurrence of the peak. For example, a waveform whose intensity increases two successive times may be determined as constituting the pulse wave.

Then, the correct position detection signal Ms is output after determining, based on the result of the statistical processing, whether the correct position is reached or not. The correct position detection signal Ms may be represented, for example, by three different levels, 1, 2, and 3, for different degrees of correctness of the position. For example, the degree of correctness may be divided into three levels according to the intensity of the peak. The degree of correctness can be determined such that the position where the intensity of the peak is highest, for example, is the correct position, and the position where the intensity is weaker is slightly displaced from the correct position. The degree of correctness need not necessarily be divided into three levels, but may be divided in other ways. It is of course possible to set one or more threshold values for the signal strength of each frequency component plotted along the vertical axis, and the degree of correctness may be determined according to which threshold value is exceeded. In this case, the threshold value may be set in advance, or alternatively, the pulse wave data Po may be statistically processed and the threshold value may be computed based on the tendency of its occurrence.

As previously described, the operation of the second movement detection means 24 is controlled by the first moving state completion signal Ds output from the signal saturation detection unit 23 provided in the first movement detection means 25. Accordingly, the operation of the second movement detection means 24 is not started until the first moving state completion signal Ds is input. This ensures that the detection of the second moving state is performed only after the detection of the first moving state is done.

The measurement condition memory 244 stores the correct position detection signal Ms by associating it with the pulse wave data Po and, when a comparison with the past data, for example, is needed, outputs the stored data as the correct position memory signal Mss to the blood pressure measuring means 3.

Next, the operation of the blood pressure measuring means 3 will be described with reference to FIG. 3.

In FIG. 3, the blood pressure measurement determining unit 245 in the correct position detecting means 2 determines the degree to which the arm-worn blood pressure monitor 1 worn on the wrist of the subject 8 is positioned correctly with respect to the height position of the heart, and supplies the correct position detection signal Ms representing the degree of correctness to the blood pressure measurement control unit 37 in the blood pressure measuring means 3.

The blood pressure measurement control unit 37 passes the correct position detection signal Ms to the display unit 41 in the annunciating means 4. The pulse condition display section 415a provided in the measurement condition display section 415 of the display unit 41 displays a mark such as "O", "Δ", or "X" according to the level of the correct position detection signal Ms having, for example, three levels.

The blood pressure measurement control unit 37 also passes the correct position detection signal Ms to the annunciating unit 42 in the annunciating means 4. The annunciating unit 42 produces an annunciation by using a voice message such as "The blood pressure monitor is in the correct position" or "The blood pressure monitor is not in the correct position" according to the level of the correct position detection signal Ms.

The annunciating unit 42 may produce an annunciation by using a device that produces different tones for three different levels of the correct position detection signal Ms or by using a vibration motor that produces different kinds of vibrations for three different levels of the correct position detection signal Ms.

Then, based on the correct position detection signal Ms, the blood pressure measurement control unit 37 controls the blood pressure measurement in the following manner.

It is assumed that level 3 indicates that the arm-worn blood pressure monitor 1 is in the correct position. When the correct position detection signal Ms of level 3 is input, the blood pressure measurement control unit 37 outputs a pressure control signal Kc to the pressure control unit 34. Based on the pressure control signal Kc, the pressure control unit 34 outputs a pressure drive signal Kd for controlling the pressure pump 33. In response to the pressure drive signal Kd from the pressure control unit 34, the pressure pump 33 provides pressure for inflating the cuff 31.

The pressure inside the cuff 31 is constantly detected by the pressure sensor 32 which outputs the detected value to the blood pressure measurement control unit 37. When the cuff 31 is inflated to a predetermined pressure, the blood pressure measurement control unit 37 controls the pressure control unit 34 to stop the operation of the pressure pump 33.

The blood pressure measurement control unit 37 outputs a bleeder control signal Hc to the bleeder control unit 36. Based on the bleeder control signal Hc, the bleeder control unit 36 outputs a bleeder drive signal Hd for controlling the bleeder valve 35.

Based on the bleeder drive signal Hd, the bleeder valve 35 bleeds the pressure from the cuff 31 in such a manner that the pressure inside the cuff 31 decreases at a constant rate over time. As the pressure inside the cuff 31 gradually decreases, a pressure oscillometric waveform (not shown) based on the so-called oscillometric theory is generated inside the cuff 31 in accordance with the blood pressure in the wrist of the subject 8. The pressure sensor 32 detects the pressure oscillometric waveform.

The blood pressure measurement control unit 37 detects blood pressure information Kj, such as the systolic blood pressure, diastolic blood pressure, and pulse rate, from the pressure oscillometric waveform of the pressure signal So output from the pressure sensor 32. The blood pressure measurement control unit 37 stores the detected blood pressure information Kj in the blood pressure information memory 371; the detected blood pressure information Kj is also output to the display unit 41 in the annunciating means 4.

Next, a description will be given of how the correct position is monitored during blood pressure measurement.

There can occur cases where the position of the arm-worn blood pressure monitor 1 becomes displaced from the height position of the heart during blood pressure measurement. Even when the blood pressure measurement is started in the correct position, if the arm is displaced from the correct position during the blood pressure measurement because, for example, the arm sags, the measured blood pressure value will be rendered unreliable. If the subject has unintentionally moved his arm out of the correct position in this way, the subject may think that the blood pressure measurement has been properly measured when actually the blood pressure measurement has not been properly measured.

To avoid such a situation, the arm-worn blood pressure monitor 1, after starting the blood pressure measurement in the correct position, can continue to perform microwave sensing so that it can monitor whether the arm is properly held in the correct position during the blood pressure measurement. More specifically, even after the blood pressure measurement is started after completion of the second moving state, the arm-worn blood pressure monitor 1 constantly monitors the peak of the pulse wave data Po and outputs the correct position detection signal Ms. When a change occurs in the correct position detection signal Ms, an annunciation is produced by using the annunciating means 4. For example, a message "Displaced from the correct position" is produced. When a substantial change occurs in the level of the correct position detection signal Ms, the blood pressure measurement is stopped. For example, when the level has changed from the level 3 that indicates the position being in the correct position to the level 1 indicating the position being displaced from the correct position, the arm-worn blood pressure monitor 1 stops the blood pressure measurement by causing the annunciating means 4 to produce a message "Blood pressure measurement is stopped".

However, there are cases where the subject wants to know his blood pressure value, even though his arm is not placed in the correct position for some reason. In such cases, the subject can forcefully start the blood pressure measurement by operating the measurement start switch or the like on the operation unit.

Next, the operation flow of the blood pressure measurement performed by the arm-worn blood pressure monitor 1 will be described below by referring primarily to FIG. 5. FIG. 5 is a flowchart illustrating the operation flow from the time the arm-worn blood pressure monitor 1 is worn on the wrist to the time the blood pressure measurement is completed. The flow shown in FIG. 5 is carried out under the control of a CPU of the blood pressure measurement control unit 27 in accordance with a program prestored in a memory maintained in the blood pressure measurement control unit 27.

First, the subject 8 wears the arm-worn blood pressure monitor 1 on his wrist and presses the measurement start switch on the operation unit (S1).

Thereupon, the correct position detecting means 2 shown in FIG. 3 starts the microwave sensing operation (S2).

Next, a determination is made as to whether the first moving state is completed or not (S3). The subject 8 moves his wrist with the arm-worn blood pressure monitor 1 worn thereon toward the front part of his chest (first moving state).

During that time, the signal saturation detection unit 23 counts the number of times that the amplitude of the digital signal Do exceeds the prescribed amplitude range Dr. Based on the count of the number of times, it is determined whether the first moving state is completed or not. That is, when a large arm motion stops, the amplitude of the digital signal Do settles within the prescribed amplitude range Dr, and the first moving state is thus completed. When the first moving state is completed, the signal saturation detection unit 23 outputs the first moving state completion signal Ds.

As this time, though not explicitly shown in FIGS. 3 and 5, the first moving state completion signal Ds from the signal saturation detection unit 23 is input to the blood pressure measurement control unit 37. Based on the first moving state completion signal Ds, the blood pressure measurement control unit 37 may control the annunciating unit 42 in the annunciating means 4 to annunciate the completion of the first moving state by means of sound or light or a voice message such as "The blood pressure monitor is placed in the correct position".

If the subject 8 has moved his wrist not close enough to his chest or not in a proper manner, it is determined based on the measuring condition of the signal saturation detection unit 23 that the first moving state is not completed yet.

If it is determined in S3 that the first moving state is not completed yet, the annunciating unit 42 in the annunciating means 4 is controlled to produce a voice annunciation such as "The blood pressure monitor is not in the correct position" or "Move the blood pressure monitor closer to your chest once again" (S3'). Step S3' is performed by the blood pressure measurement control unit 37 when the first moving state is not completed within three seconds after the measurement start switch has been pressed. The reason that the time interval is set to three seconds is that usually the blood pressure monitor is moved to the position of the chest in about one second after the measurement start switch has been pressed. However, the time interval need not be limited to three seconds.

After producing the voice annunciation prompting the subject to move the arm-worn blood pressure monitor 1 closer to his chest, the process returns to S3 to detect the first moving state. The process of S3 and S3' is repeated until the completion of the first moving state is detected.

If it is determined in S3 that the first moving state is completed, the FFT processing unit 242 in the second movement detecting means 24 accumulates the digital signal Do over the predetermined time interval in accordance with the second time information T2 (S4).

Next, the FFT processing unit 242 computes the fundamental wave Bf by fast-Fourier transforming the digital signal Do accumulated over the predetermined time interval (S5). Since the FFT processing involves a large computational burden, the processing is performed, not by the blood pressure measurement control unit 37, but by a CPU of the FFT processing unit 242 in the second movement detecting unit 24.

Next, the blood pressure measuring means 3 makes a determination as to whether the second moving state is completed or not (S6). The pulse wave detection unit 243 in the blood second moving state detecting means 24 shown in FIG. 3 outputs the pulse wave data Po by extracting it from the fundamental wave Bf. If it is assumed, based on experiment, etc., that the frequency spectral distribution of the pulse wave is from 0.5 Hz to 3.0 Hz, then it can be determined that the arm-worn blood pressure monitor 1 positioned on the front part of the chest is at the same height as the heart when the pulse wave data Po lying within that frequency range is detected. The blood pressure measurement determining unit 245 analyzes the received pulse wave data Po, and outputs the correct position detection signal Ms to the blood pressure measuring means 3. Based on the received correct position detection signal Ms, the blood pressure measuring means 3 determines whether the second moving state is completed or not. More specifically, when the correct position detection signal Ms of level 3 is received, it is determined that the second moving state is completed, but when the correct position detection signal Ms of level 2 or level 1 is received, it is determined that the second moving state is not yet completed.

If it is determined in S6 that the second moving state is completed, the microwave sensing operation is terminated, and the blood pressure measuring means 3 starts the blood pressure measurement (S7).

If it is determined in S6 that the second moving state is not yet completed, the blood pressure measuring means 3 controls the annunciating means 4 and causes the annunciating unit 42 to produce an annunciation accordingly by using a buzzer sound or mark that differs according to the degree of correctness of the position relative to the height position of the heart (S6').

If the blood pressure measurement determining unit 245 is unable to detect the pulse wave data Po because the arm-worn blood pressure monitor 1 positioned on the front part of the chest is not at the same height as the heart, the blood pressure measurement control unit 37 produces an alarm sound or an alarm display, based on the correct position detection signal Ms. For example, an annunciation such as "Move the blood pressure monitor further upward" or "Move the blood pressure monitor further downward" is produced by using the annunciating means 4.

Further, if the arm-worn blood pressure monitor 1 positioned on the front part of the chest is a little too far away from the heart, the pulse wave data Po may not be detected. In this case, an annunciation such as "Move the blood pressure monitor closer to the chest" is produced. After producing the annunciation prompting the subject to move the arm-worn blood pressure monitor 1 to the position at the same height as the heart, the process returns to S4 to repeat the process from S4 to S6' until the completion of the second moving state is detected.

Next, by controlling the pressure control unit 34 and the bleeder control unit 36 as earlier described, the blood pressure measurement control unit 37 in the blood pressure measuring means 3 obtains the blood pressure information Kj, such as the systolic blood pressure, diastolic blood pressure, and pulse rate, from the pressure oscillometric waveform of the pressure signal So output from the pressure sensor 32, after which the blood pressure measurement is terminated (S8).

Alternatively, the correct position detection signal Ms may be constantly monitored during the blood pressure measurement without terminating the microwave sensing operation after the second moving state is completed (S7'). In this case, an annunciation is generated using the annunciating means 4 to provide an indication according to the result of the monitoring of the correct position detection signal Ms during the blood pressure measurement. For example, if the arm-worn blood pressure monitor 1 is displaced from the correct position during the blood pressure measurement, an annunciation to that effect is generated, and the blood pressure measurement is stopped to terminate the process (S8').

When the blood pressure measurement is completed, the blood pressure information, such as the systolic blood pressure, diastolic blood pressure, and pulse rate, and the correct position detection signal Ms are stored in the blood pressure information memory 371 maintained in the blood pressure measurement control unit 37 (S9). On the other hand, the annunciating means 4 annunciates the information stored in the blood pressure information memory 371.

The subject presses the measurement start switch on the operation unit to terminate the series of measuring operations (S10).

Since the arm can be correctly guided to the correct position using the microwave Doppler sensor, as described above, the arm-worn blood pressure monitor 1 can measure the blood pressure in the correct position and can record the pulse rate, which is said to represent the physically resting state or mentally stable state of the subject before the blood pressure measurement, so that the recorded information can be presented for viewing anytime after the blood pressure measurement.

That is, the arm-worn blood pressure monitor 1 can not only prove that the blood pressure has been measured under proper measurement conditions, but can also record the condition of the subject along with the measured blood pressure values.

Using the arm-worn blood pressure monitor 1, changes in the physically resting state or mentally stable state of the subject can be kept track of in detail, for example, when examining variations in the blood pressure measured a plurality of times under 24-hour ambulatory conditions.

Next, an alternative arm-worn blood pressure monitor 10 will be described with reference to FIGS. 7 to 9.

The alternative arm-worn blood pressure monitor 10 differs from the arm-worn blood pressure monitor 1 in that the alternative arm-worn blood pressure monitor 10 further includes a respiratory wave detection unit 246 which detects the respiration rate of the subject. That is, not only is the position of the arm-worn blood pressure monitor 10 relative to the height position of the heart is detected by microwave sensing, but the wave components associated with the subject's respiration is also detected so that the physical resting state of the subject can be detected more accurately by also taking respiratory information into account.

In the description of the arm-worn blood pressure monitor 10, the same component elements as those of the arm-worn blood pressure monitor 1 are designated by the same reference numerals, and such component elements will not be further described herein.

Figure 7:
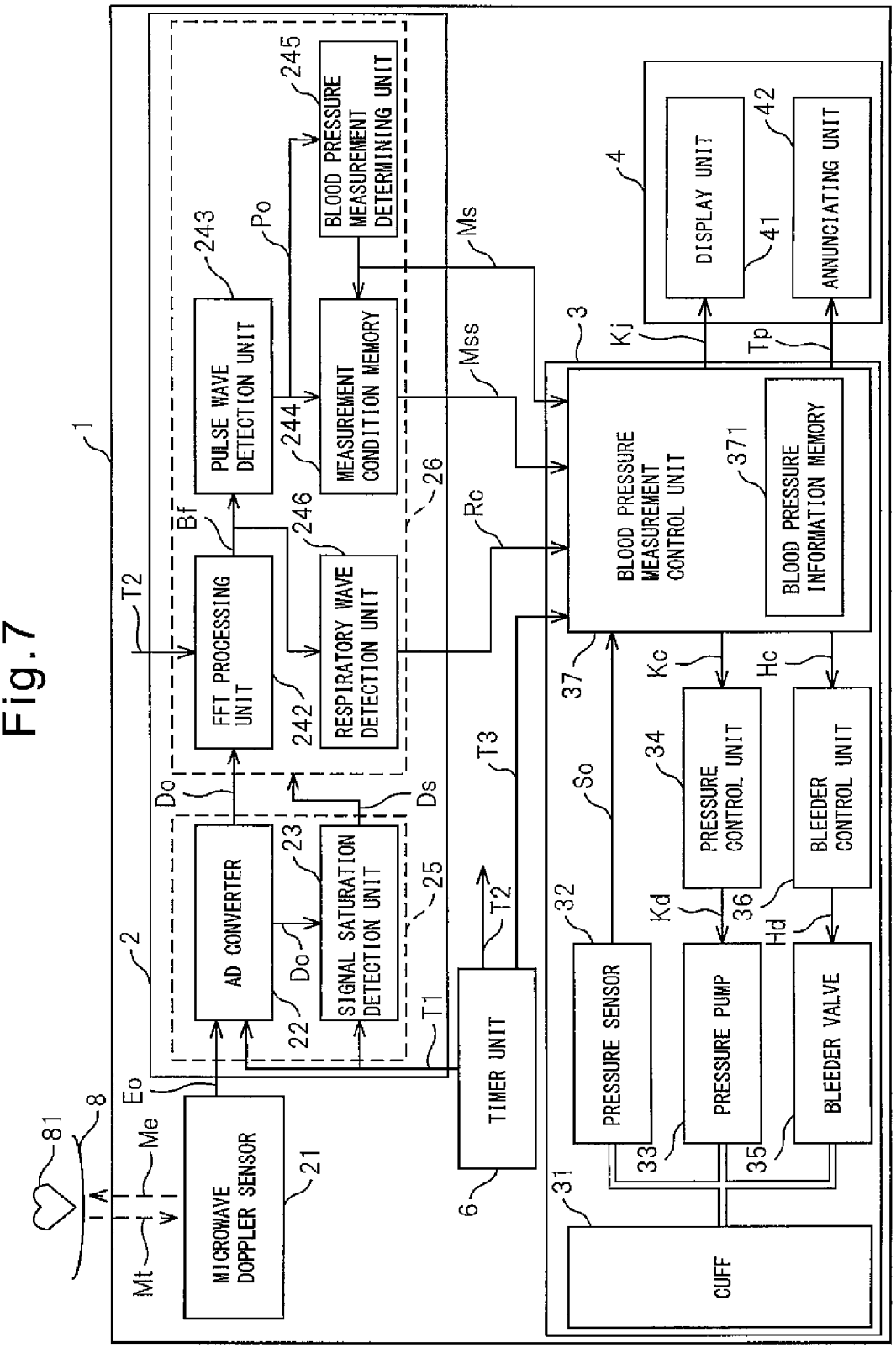
FIG. 7 is a functional block diagram showing the configuration of an alternative arm-worn blood pressure monitor 10.

FIG. 7 is a functional block diagram of the alternative arm-worn blood pressure monitor 10. FIG. 9 is a diagram for explaining display examples produced on the arm-worn blood pressure monitor 10.

As shown in FIG. 7, the second movement detecting means 26 in the correct position detecting means 2 includes the respiratory wave detection unit 246. The respiratory wave detection unit 246 takes as input the fundamental wave Bf output from the FFT processing unit 242, extracts respiration-related information from the fundamental wave Bf, and outputs the extracted information as respiratory wave data Rc to the blood pressure measurement control unit 37 in the blood pressure measuring means 3.

As shown in FIG. 9, the display unit 41 includes a respiration rate display section 414 in addition to the systolic blood pressure display section 411, the diastolic blood pressure display section 412, the pulse rate display section 413, the measurement condition display section 415 which includes a respiration condition display section 415b in addition to the pulse condition display section 415a, and the date/time display section 416 for displaying information indicating the date and time of blood pressure measurement.

The display unit 41 displays the blood pressure information Kj, including the systolic blood pressure, diastolic blood pressure, pulse rate, and correct position detection signal Ms, that the blood pressure measurement control unit 37 in the blood pressure measuring means 3 outputs.

Figure 9A:
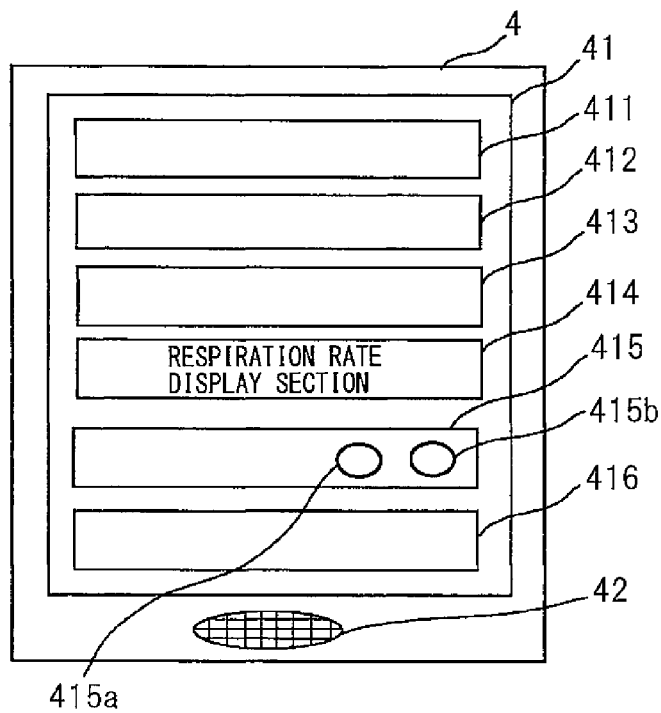
FIGS. 9(a) and 9(b) are diagrams for explaining display examples produced on the arm-worn blood pressure monitor shown in FIG. 7.
Figure 9B:
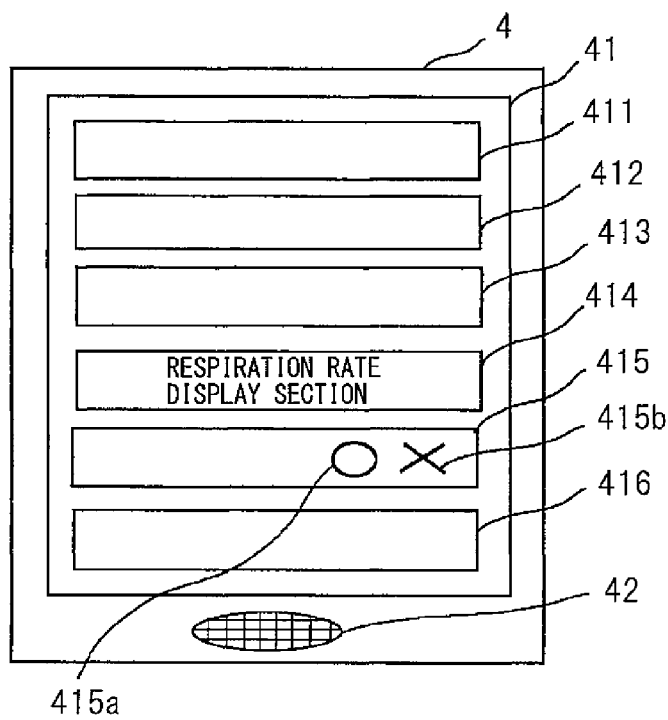
Figure 10A:
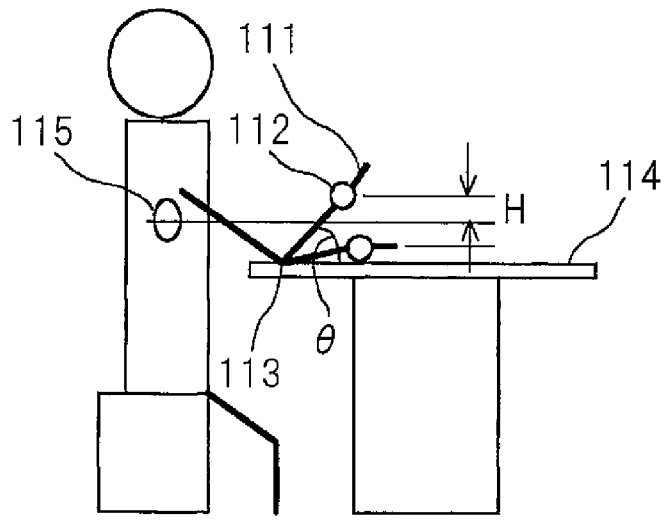
FIGS. 10(a) to 10(c) are diagrams for explaining a wrist-worn blood pressure monitor disclosed in patent document 1.
Figure 10B:
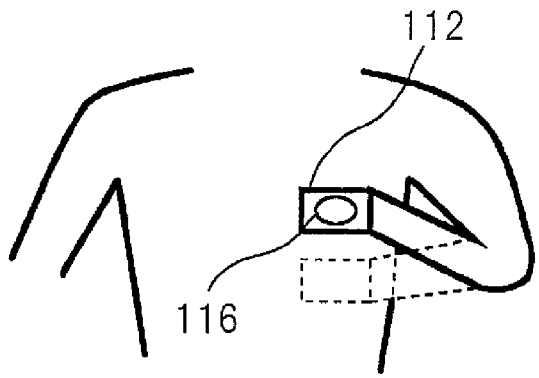
Figure 10C:
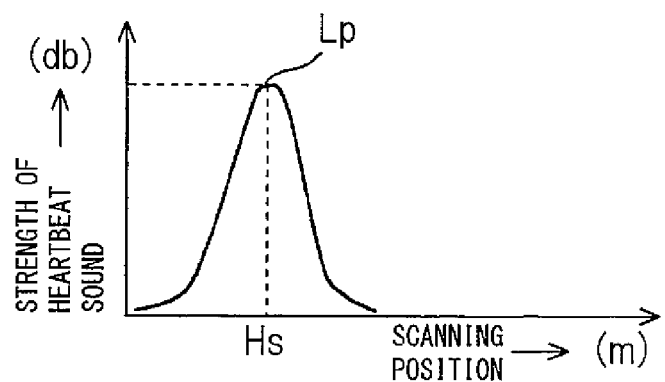

FIG. 9(a) shows an example of the display produced when the respiratory wave data Rc has been input, and FIG. 9(b) shows an example of the display produced when the respiratory wave data Rc has not been input. The respective conditions are indicated by marks "O" and "X", respectively, in the respiration condition display section 415b.

Next, the operation of the arm-worn blood pressure monitor 10 will be described with reference to FIGS. 7 to 9.

Figure 8A:
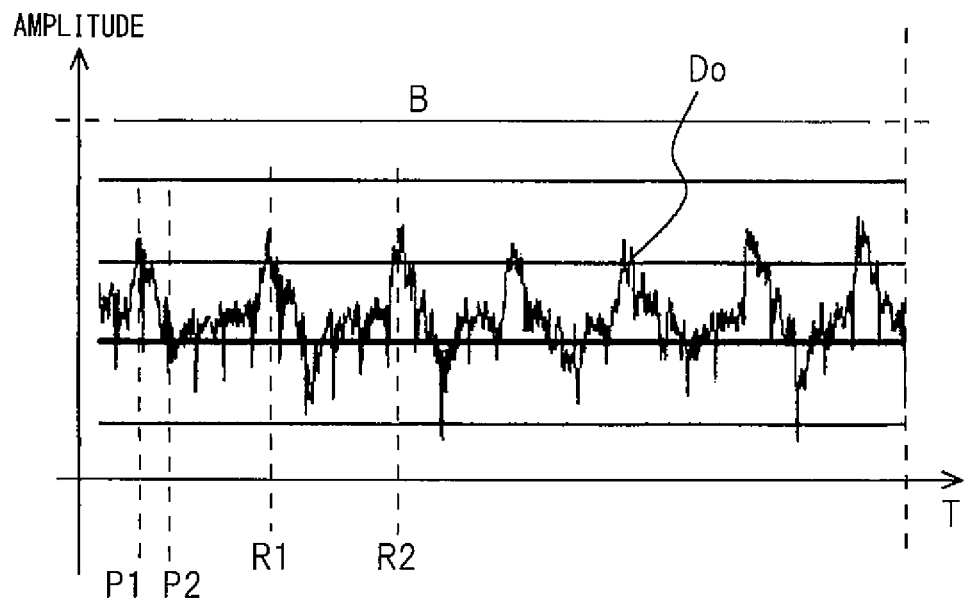
FIGS. 8(a) and 8(b) are waveform diagrams for explaining the operation of the arm-worn blood pressure monitor shown in FIG. 7.
Figure 8B:
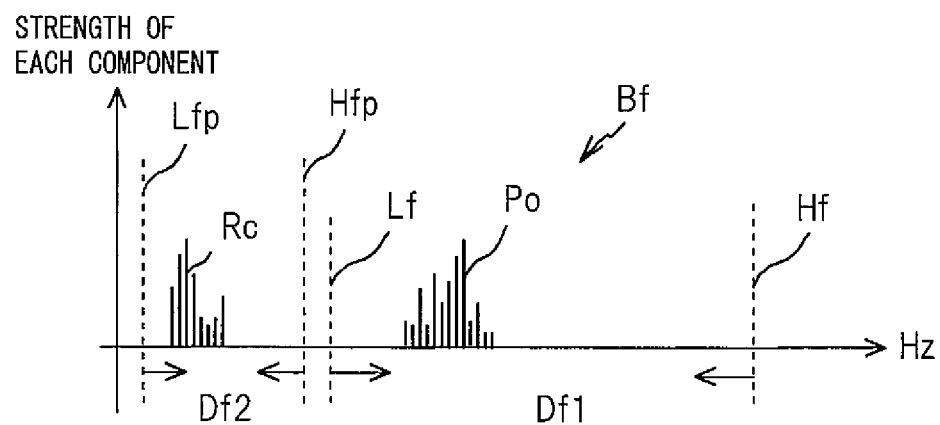

FIG. 8 is a waveform diagram for explaining the operation of the second movement detecting means 26 in the correct position detecting means 2. In FIG. 8, FIG. 8(a) corresponds to FIG. 4(b), and FIG. 8(b) corresponds to FIG. 4(c).

As previously described, the interval B in FIG. 4(a) represent the time interval during which the wrist is placed and held in position near the heart; this time interval represents the second moving state shown in FIGS. 2(d) and 2(e). In the interval B, since the arm is no longer being moved with a large motion but is being moved with a small motion in order to search for the correct position, the digital signal Do whose amplitude falls within the prescribed amplitude range Dr is detected. The waveform in this interval B contains a waveform associated with the beating of the heart and a waveform associated with the respiration accompanied by the movement of the chest.

FIG. 8(a) is a diagram showing in enlarged form a portion of the digital waveform Do in the interval B depicted in FIG. 4(a). The digital signal Do shown in FIG. 8(a) also contains the components (for example, R1 and R2) associated with the respiration of the subject 8.

FIG. 8(b) is a diagram schematically illustrating the waveform obtained by fast-Fourier transforming the digital signal Do by the FFT processing unit 242, and shows a frequency spectral distribution diagram. This waveform is the fundamental wave Bf.

The second movement detecting means 26 computes the pulse wave data Po and the respiratory wave data Rc each from a prescribed frequency range of the fundamental wave Bf.

In FIG. 8(b), Lfp is a third frequency threshold value, and Hfp is a fourth frequency threshold value. The range bounded by the third frequency threshold value Lfp and the fourth frequency threshold value Hfp is the prescribed frequency range Dfl2. This frequency range must be set so as to be able to capture the respiration. According to the result of the experiment conducted by the present inventor, when the third frequency threshold value Lfp is set at 0.06 Hz and the fourth frequency threshold value Hfp at 0.4 Hz, the respiration in the resting state can be captured. These values are only examples, and the third frequency threshold value Lfp and the fourth frequency threshold value Hfp are not limited to any specific values.

The pulse wave detection unit 243 outputs the pulse wave data Po by extracting the frequency spectral distribution contained in the prescribed frequency range Df1 of the fundamental wave Bf. When the pulse wave data Po is detected properly, the second moving state is completed. At this time, the arm-worn blood pressure monitor 10 is located in the correct position at the same height as the heart 81, as shown in FIG. 2(e), as previously described. In this case, the respiratory wave data Rc has no relevance to the detection of the second moving state.

The blood pressure measurement control unit 37 in the blood pressure measuring means 3 takes as input the respiratory wave data Rc output from the respiratory wave detection unit 246, in addition to the pressure signal So output from the pressure sensor 32 and the correct position detection signal Ms output from the blood pressure measurement determining unit 245 in the correct position detecting means 2.

The blood pressure measurement control unit 37, based on the respiratory wave data Rc, displays the respiration rate per minute in the respiration rate display section 414 of the display unit 41, while also displaying, for example, a mark "O" in the respiration condition mark display section 415b provided in the measurement condition display section 415. If the respiratory wave data Rc has not been input, a mark "X", for example, is displayed in the respiration condition mark display section 415b.

The blood pressure measurement control unit 37 in the blood pressure measuring means 3 may perform control considering the safety of respiration by making provisions, for example, not to start the blood pressure measurement until the respiratory wave data Rc being output from the respiratory wave detection unit 246 settles within a predetermined range (for example, a range bounded by a maximum value Rch and a minimum value Rcl).

In addition to the raw data such as the above-mentioned respiration rate and respiration period, various statistical indices such as the mean values, standard deviations, etc., of the respiration rate and respiration period may be used as the respiratory wave data Rc.

When all the conditions for blood pressure measurement are ready, the blood pressure measurement control unit 37 in the blood pressure measuring means 3 controls the annunciating unit 42 in the annunciating means 4 to produce an annunciation using a buzzer sound or the like to annunciate that the blood pressure measurement can be started, and thus starts to measure the blood pressure.

Next, the operation flow of the blood pressure measurement performed by the arm-worn blood pressure monitor 10 will be described below.

The operation flow of the blood pressure measurement performed by the arm-worn blood pressure monitor 10 is identical to the operation flow of the blood pressure measurement performed by the arm-worn blood pressure monitor 1 in FIG. 5, with the exception of steps S6 and S9 shown in the flow of FIG. 5, and the other steps are the same. Therefore, the following describes only the operation flow of the arm-worn blood pressure monitor 10 corresponding to the steps S6 and S9 shown in the flow of FIG. 5.

In the blood pressure measurement operation flow of the arm-worn blood pressure monitor 10, while the second moving state is being detected in S6, the respiratory wave detection unit 246 in the second movement detecting means 26 shown in FIG. 7 detects as the respiratory wave data Rc the frequency components lying within the range of 0.06 Hz to 0.4 Hz, i.e., the range bounded by the third frequency threshold value and the fourth frequency threshold value.

Further, in the blood pressure measurement operation flow of the arm-worn blood pressure monitor 10, the blood pressure measurement control unit 37 in S9 stores the blood pressure values and measurement conditions in the blood pressure information memory 371 along with the respiratory wave data Rc that the respiratory wave detection unit 246 detected while the second moving state was being detected as described above.

As has been described above, according to the arm-worn blood pressure monitor 10, by performing the blood pressure measurement in the correct position and by measuring and recording the respiration rate in addition to the pulse rate which is said to represent the physically resting state or mentally stable state of the subject before the blood pressure measurement, the recorded information can be presented for viewing anytime after the blood pressure measurement.

That is, the arm-worn blood pressure monitor 10 can not only prove that the blood pressure has been measured under proper measurement conditions and is therefore reliable, but also can record the condition of the subject along with the measured blood pressure values. For example, when examining variations in the blood pressure measured a plurality of times under 24-hour ambulatory conditions, changes in the physically resting state or mentally stable state of the subject can be kept track of in detail.

While the arm-worn blood pressure monitor 1 and the arm-worn blood pressure monitor 10 have been respectively described above, it is of course possible to make changes without departing from the spirit and scope of the present invention.

For example, in the arm-worn blood pressure monitor 1 and the arm-worn blood pressure monitor 10, the subject's normal pulse rate and respiration rate may be recorded in advance in the blood pressure information memory 371 maintained in the blood pressure measurement control unit 37. Further, in the arm-worn blood pressure monitor 1 and the arm-worn blood pressure monitor 10, it is also possible to record the subject's average pulse rate and average respiration rate by calculating them from the past measurements. In this case, the currently measured pulse rate, respiration rate, etc., may be compared with the previously recorded pulse rate, respiration rate, etc., during blood pressure measurement, and an annunciation such as "The pulse rate is higher than normal" or "The respiration rate is higher than normal" may be produced by using the annunciating means 4.

With the above processing, the subject can recognize his current physical condition, etc. For example, if the subject is put in a physically strained position, for example, with his arm being bent unconsciously in an awkward manner during the blood pressure measurement, a pulse rate or respiration rate higher than normal may be detected. In such cases, the subject can be guided to take a correct position for blood pressure measurement by producing an annunciation such as "Please relax" or "Please put yourself in a correct position for blood pressure measurement".

In the above description, the arm-worn blood pressure monitor 1 and the arm-worn blood pressure monitor 10 have each been shown as being worn on the wrist, but may of course be worn on the upper arm. Further, while the above description has been given by taking as an example the configuration in which the cuff is integrated with the main body of the blood pressure monitor, it will be appreciated that such parts may be provided as separate parts, the only requirement being that the cuff and the microwave Doppler sensor be combined in one unit.

What is important is that the body part around which the cuff of the arm-worn blood pressure monitor is worn for blood pressure measurement be positioned at the same height as the heart, and that the blood pressure measurement be made with the subject put in a position that does not physically strain. Further, if the position does not physically strain, it is also important for the blood pressure measurement that the subject take care not to put himself in an awkward position by, for example, unnecessarily raising his arm.

The arm-worn blood pressure monitor 1 and the arm-worn blood pressure monitor 10 can each be used as a wrist-worn blood pressure monitor because, even when worn on the wrist, the blood pressure can be measured correctly. In the case of the wrist-worn blood pressure monitor, the blood pressure monitor is non-encumbering and suitable to be worn continuously for long periods, and therefore, the blood pressure can be measured repeatedly a plurality of times over extended periods, the device thus being also advantageous for use as a blood pressure monitor for discovering masked hypertension, etc.

What is claimed is:

1. A blood pressure monitor comprising:
a cuff to be worn around an arm of a human subject;
a microwave transmitting unit for radiating a microwave onto said human subject;
a microwave receiving unit for receiving a reflected wave Doppler-shifted relative to said radiated microwave due to a heartbeat of said subject; and
a correct position detector for detecting, based on said reflected wave, whether said cuff is located in a correct position relative to a position of the heart of said human subject,
said correct position detector including,
a first movement detector for detecting a first moving state in which said cuff is being moved toward a front part of a chest of said subject, based on an amplitude of a phase difference signal representing a phase difference between a transmitted microwave signal corresponding to said microwave radiated by said microwave transmitting unit and a received microwave signal corresponding to said reflected wave received by said microwave receiving unit, and
a second movement detector for detecting a second moving state in which said cuff is being moved toward said correct position on the front part of said chest, based on signal frequency components of said phase difference signal.

2. The blood pressure monitor according to claim 1, wherein after it is determined by said first movement detector that said first moving state is completed, said second movement detector detects said second moving state.

3. The blood pressure monitor according to claim 2, wherein said first movement detector detects said first moving state by detecting from said phase difference signal any signal whose amplitude exceeds a prescribed amplitude range, and
said second movement detector performs Fourier transform processing by accumulating over a predetermined time interval said phase difference signal whose amplitude does not exceed said prescribed amplitude range, extracts a fundamental wave of signal components, and detects said second moving state by extracting, as a pulse wave, signal components of said fundamental wave that fall within a prescribed frequency range.

4. The blood pressure monitor according to claim 3, wherein said first movement detector includes an AD converter for converting said phase difference signal into digital form for output, and a signal saturation state detector,
said AD converter converts said phase difference signal into a digital signal by sampling said phase difference signal based on first time information, and
said signal saturation state detector counts, based on said digital signal, the number of occurrences of amplitude saturation exceeding said prescribed amplitude range bounded by a first saturation threshold value and a second saturation threshold value, wherein when the number of occurrences of said amplitude saturation is larger than a predetermined number, it is determined that said first moving state is in progress and, when the number of occurrences of said amplitude saturation decreases to zero after it is determined that said first moving state is in progress, it is determined that said first moving state is completed; and
said second movement detector includes an FFT unit for performing said Fourier transform processing, and a pulse wave detector,
said FFT unit performs said Fourier transform processing by accumulating said digital signal over said predetermined time interval based on second time information, and thereby extracts said fundamental wave of signal components, and
said pulse wave detector, based on said fundamental wave, extracts as said pulse wave said signal components that fall within said prescribed frequency range bounded by a first frequency threshold value and a second frequency threshold value, and determines, upon detection of said pulse wave, that said cuff has been moved to said correct position.

5. The blood pressure monitor according to claim 4, wherein said second movement detector further includes a blood pressure measurement determining unit for determining whether said cuff is located in said correct position, and a blood pressure measuring unit, and
when it is determined by said blood pressure measurement determining unit that said cuff has been moved to said correct position, said blood pressure measuring unit starts blood pressure measurement.

6. The blood pressure monitor according to claim 5, further comprising:
a timer;
a memory; and
an alarm for annunciating information by means of a display, sound, light, vibration, or a combination thereof, and
wherein date/time information obtained from said timer, information related to said pulse wave, and a result of said blood pressure measurement are stored in said memory, and contents stored in said memory are annunciated by using said alarm.

7. The blood pressure monitor according to claim 6, wherein when it is determined by said blood pressure measurement determining unit that said cuff has been moved to said correct position, said alarm annunciates that said cuff is located in said correct position.

8. The blood pressure monitor according to claim 6, wherein said second movement detector extracts respiration information from said phase difference signal when detecting said second moving state, and stores said respiration information in said memory along with said date/time information obtained from said timer, said information related to said pulse wave, and the result of said blood pressure measurement.

9. The blood pressure monitor according to claim 4, wherein if said cuff is displaced from said correct position after said blood pressure measurement has been started, said blood pressure measuring unit stops said blood pressure measurement.

* * * * *